United States Patent [19]

Lok et al.

[11] Patent Number: 4,935,216

[45] Date of Patent: * Jun. 19, 1990

[54] ZINC-ALUMINUM-PHOSPHORUS-SILICON-OXIDE MOLECULAR SIEVE COMPOSITIONS

[75] Inventors: Brent M. T. Lok, New City; Lawrence D. Vail, New Rochelle; Edith M. Flanigen, White Plains, all of N.Y.

[73] Assignee: UOP, Des Plaines, Ill.

[*] Notice: The portion of the term of this patent subsequent to Dec. 27, 2005 has been disclaimed.

[21] Appl. No.: 600,170

[22] Filed: Apr. 13, 1984

[51] Int. Cl.$^5$ .............................................. C01B 33/28
[52] U.S. Cl. ...................................... 423/328; 423/593
[58] Field of Search ............... 423/305, 306, 326, 328, 423/329; 502/60, 62, 77, 162, 164, 208, 214; 428/593

[56] References Cited

U.S. PATENT DOCUMENTS

| | | | |
|---|---|---|---|
| 3,941,871 | 3/1976 | Dwyer et al. | 423/326 |
| 4,310,440 | 1/1982 | Wilson et al. | 423/305 X |
| 4,420,467 | 12/1983 | Whittam | 423/328 |
| 4,440,871 | 4/1984 | Lok et al. | 502/214 |
| 4,456,582 | 6/1984 | Marosi et al. | 423/328 X |
| 4,486,397 | 12/1984 | Eshraghi et al. | 423/306 |
| 4,500,651 | 2/1985 | Lok et al. | 502/208 |
| 4,567,029 | 1/1986 | Wilson et al. | 502/208 |

FOREIGN PATENT DOCUMENTS

| | | |
|---|---|---|
| 0054364 | 6/1982 | European Pat. Off. . |
| 0055046 | 6/1982 | European Pat. Off. . |
| 0055529 | 7/1982 | European Pat. Off. . |
| 0059059 | 9/1982 | European Pat. Off. . |

OTHER PUBLICATIONS

Schmitz-DuMont "Zeitschrift fur Anorganische und Allgemeine Chemie" 302, 1959, pp. 121–135.

*Primary Examiner*—John Doll
*Assistant Examiner*—R. Bruce Breneman
*Attorney, Agent, or Firm*—Thomas K. McBride; Eugene I. Snyder; Frank S. Molinaro

[57] ABSTRACT

Crystalline molecular sieves having three-dimentional microporous framework structures of $ZnO_2$, $AlO_2$, $SiO_2$ and $PO_2$ tetrahedral units are disclosed. These molecular sieves have an empirical chemical composition on an anhydrous basis expressed by the formula:

$$mR: (Zn_wAl_xP_ySi_z)O_2$$

wherein "R" represents at least one organic templating agent present in the intracrystalline pore system; "m" represents the molar amount of "R" present per mole of $(Zn_wAl_xP_ySi_z)O_2$; and "w", "x", "y" and "z" represent the mole fractions of zinc, aluminum, phosphorus and silicon, respectively, present as tetrahedral oxides. Their use as adsorbents, catalysts, etc. is also disclosed.

28 Claims, 3 Drawing Sheets

ZINC-ALUMINUM-PHOSPHORUS-SILICON-OXIDE MOLECULAR SIEVE COMPOSITIONS

FIELD OF THE INVENTION

The instant invention relates to a novel class of crystalline microporous molecular sieves, to the method of their preparation. The invention-oxide relates to novel zinc-aluminum-phosphorus-silicon molecular sieves having zinc, aluminum, phosphorus and silicon in the form of framework tetrahedral oxides. These compositions may be prepared hydrothermally from gels containing reactive compounds of zinc, aluminum, phosphorus and silicon capable of forming a framework tetrahedral oxides, and preferably at least one organic templating agent which functions in part to determine the course of the crystallization mechanism and the structure of the crystalline product.

BACKGROUND OF THE INVENTION

Molecular sieves of the crystalline aluminosilicate zeolite type are well known in the art and now comprise over 150 species of both naturally occurring and synthetic compositions. In general the crystalline zeolites are formed from corner-sharing $AlO_2$ and $SiO_2$ tetrahedra and are characterized by having pore openings of uniform dimensions, having a significant ion-exchange capacity and being capable of reversibly desorbing an adsorbed phase which is dispersed throughout the internal voids of the crystal without displacing any atoms which make up the permanent crystal structure.

Other crystalline microporous compositions which are not zeolitic, i.e. do not contain $AlO_2$ tetrahedra as essential framework constituents, but which exhibit the ion-exchange and/or adsorption characteristics of the zeolites are also known. Metal organosilicates which are said to possess ion-exchange properties, have uniform pores and are capable of reversibly adsorbing molecules having molecular diameters of about 6Å or less, are reported in U.S. Pat. No. 3,941,871 issued Mar. 2, 1976 to Dwyer et al. A pure silica polymorph, silicalite, having molecular sieving properties and a neutral framework containing neither cations nor cation sites is disclosed in U.S. Pat. No. 4,061,724 issued Dec. 6, 1977 to R. W. Grose et al.

A recently reported class of microporous compositions and the first framework oxide molecular sieves synthesized without silica, are the crystalline aluminophosphate compositions disclosed in U.S. Pat. No. 4,310,440 issued Jan. 12, 1982 to Wilson et al. These materials are formed from $AlO_2$ and $PO_2$ tetrahedra and have electrovalently neutral frameworks as in the case of silica polymorphs. Unlike the silica molecular sieve, silicalite, which is hydrophobic due to the absence of extra-structural cations, the aluminophosphate molecular sieves are moderately hydrophilic, apparently due to the difference in electronegativity between aluminum and phosphorus. Their intracrystalline pore volumes and pore diameters are comparable to those known for zeolites and silica molecular sieves.

In copending and commonly assigned application Ser. No. 400,438, filed Jul. 26, 1982, now U.S. Pat. No. 4,440,871, there is described a novel class of silicon-substituted aluminophosphates which are both microporous and crystalline. The materials have a three dimensions crystal framework of $PO_2{}^+$, $AlO_2{}^-$ and $SiO_2$ tetrahedral units and, exclusive of any alkali metal or calcium which may optionally be present, an as-synthesized empirical chemical composition on an anhydrous basis of:

$$mR:(Si_xAl_yP_z)O_2$$

wherein "R" represents at least one organic templating agent present in the intracrystalline pore system; "m" represents the moles of "R" present per mole of $(Si_xAl_yP_z)O_2$ and has a value of from zero to 0.3, the maximum value in each case depending upon the molecular dimensions of the templating agent and the available void volume of the pore system of the particular silicoaluminophosphate species involved; and "x", "y", and "z" represent the mole fractions of silicon, aluminum and phosphorus, respectively, present as tetrahedral oxides. The minimum value for each of "x", "y", and "z" is 0.01 and preferably 0.02. The maximum value for "x" is 0.98; for "y" is 0.60; and for "z" is 0.52. These silicoaluminophosphates exhibit several physical and chemical properties which are characteristic of aluminosilicate zeolites and aluminophosphates.

In copending and commonly assigned application Ser. No. 480,738, filed Mar. 31, 1983, now U.S. Pat. No. 4,500,651 there is described a novel class of titanium-containing molecular sieves whose chemical composition in the as-synthesized and anhydrous form is represented by the unit empirical formula:

$$mR:(Ti_xAl_yP_z)O_2$$

wherein "R" represents at least one organic templating agent present in the intracrystalline pore system; "m" represents the moles of "R" present per mole of $(Ti_xAl_yP_z)O_2$ and has a value of between zero and about 5.0; and "x", "y" and "z" represent the mole fractions of titanium, aluminum and phosphorus, respectively, present as tetrahedral oxides.

In copending and commonly assigned application Ser. No. 514,334, filed Jul. 15, 1983, now U.S. Pat. No. 4,567,029, there is described a novel class of crystalline metal aluminophosphates having three-dimensional microporous framework structures of $MO_2$, $AlO_2$ and $PO_2$ tetrahedral units and having an empirical chemical composition on an anhydrous basis expressed by the formula:

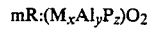

$$mR:(M_xAl_yP_z)O_2$$

wherein "R" represents at least one organic templating agent present in the intracrystalline pore system; "m" represents the moles of "R" present per mole of $(M_xAl_yP_z)O_2$ and has a value of from zero to 0.3; "M" represents at least one metal of the group magnesium, manganese, zinc and cobalt; and "x", "y" and "z" represent the mole fraction of the metal "M", aluminum and phosphorus, respectively, present as tetrahedral oxides.

In copending and commonly assigned application Ser. No. 514,335, filed Jul. 15, 1983, now U.S. Pat. No. 4,554,143, there is described a novel class of crystalline ferroaluminophosphates having a three-dimensional microporous framework structure of $FeO_2$, $AlO_2$ and $PO_2$ tetrahedral units and having an empirical chemical composition on a anhydrous basis expressed by the formula:

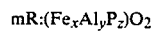

$$mR:(Fe_xAl_yP_z)O_2$$

wherein "R" represents at least one organic templating agent present in the intracrystalline pore system; "m" represents the moles of "R" present per mole of (Fe$_x$Al$_y$P$_z$)O$_2$ and has a value of from zero to 0.3; and "x", "y" and "z" represent the mole fraction of the iron, aluminum and phosphorous, respectively, present as tetrahedral oxides.

The instant invention relates to new molecular sieve compositions having framework ZnO$_2^{-2}$, AlO$_2^-$, PO$_2^+$ and SiO$_2$ as tetrahedral oxide units.

SUMMARY OF THE INVENTION

The instant invention relates to a new class of molecular sieves having a three-dimensional microporous crystal framework structures of ZnO$_2^{-2}$, AlO$_2^-$, PO$_2^+$ and SiO$_2$ tetrahedral oxide units. These new zinc-aluminum-phosphorus-silicon-oxide molecular sieves exhibit ion-exchange, adsorption and catalytic properties and, accordingly, find wide use as adsorbents and catalysts. The members of this novel class of compositions have crystal framework structures of ZnO$_2^{-2}$, AlO$_2^-$, PO$_2^+$ and SiO$_2$ tetrahedral units and have an empirical chemical composition on an anhydrous basis expressed by the formula:

wherein "R" represents at least one organic templating agent present in the intracrystalline pore system; "m" represents the molar amount of "R" present per mole of (Zn$_w$Al$_x$P$_y$Si$_z$)O$_2$ and has a value from zero to about 0.3;, and "w", "x", "y" and "z" represent the mole fractions of zinc, aluminum, phosphorus and silicon, respectively, present as tetrahedral oxides. The instant molecular sieve compositions are characterized in several ways as distinct from heretofore known molecular sieves, including the aforementioned ternary compositions. The instant molecular sieves are characterized by the enhanced thermal stability of certain species and by the existence of species heretofore unknown for binary and ternary molecular sieves.

The molecular sieves of the instant invention will be generally referred to by the acronym "ZnAPSO" to designate a crystal framework of ZnO$_2^-$, AlO$_2^-$, PO$_2^+$, SiO$_2$ and tetrahedral units. Actual class members will be identified as structural species by assigning a number to the species and, accordingly, are identified as ZnAPSO-i wherein "i" is an integer. This designation is an arbitrary one and is not intended to denote structural relationship to another material(s) which may also be characterized by a numbering system.

DETAILED DESCRIPTION OF THE INVENTION

The instant invention relates to a new class of three-dimensional microporous crystalline molecular sieves having a crystal framework structures of ZnO$_2^{-2}$, AlO$_2^-$, PO$_2^+$ and SiO$_2$ tetrahedral oxide units. These new molecular sieves exhibit ion-exchange, adsorption and catalytic properties, and accordingly find wide use as adsorbents and catalysts.

Figure 1:
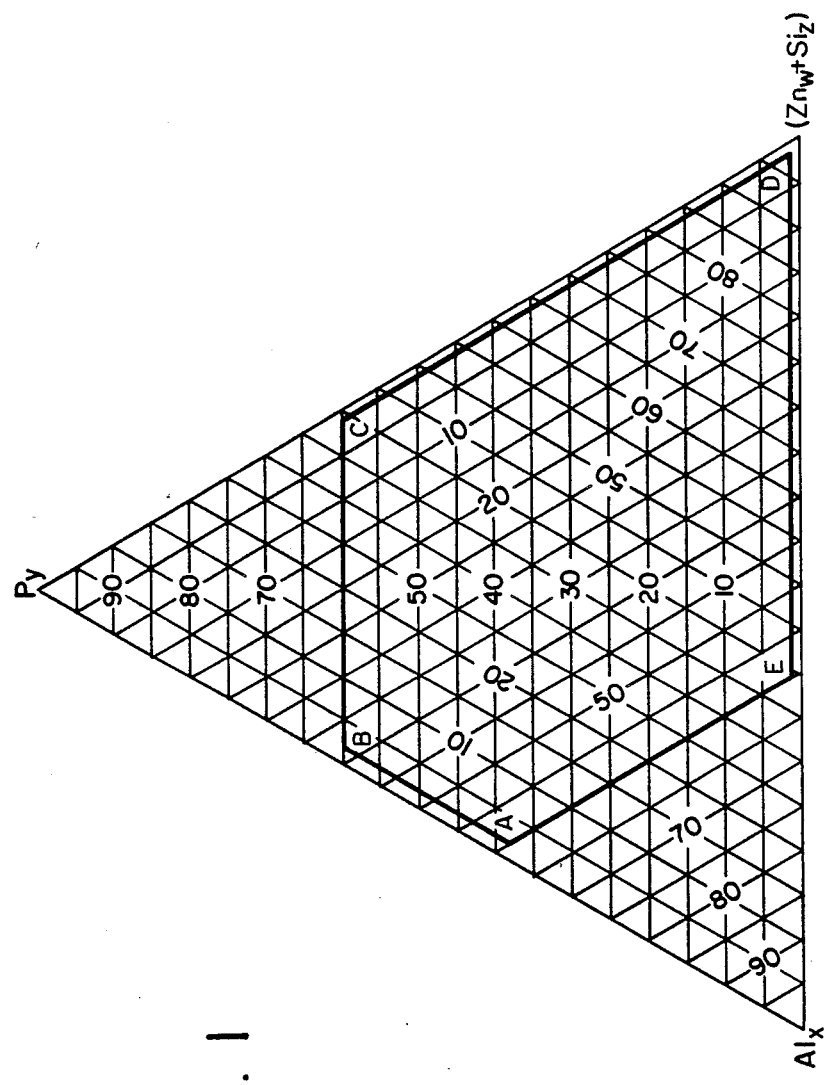
FIG. 1 is a ternary diagram wherein parameters relating to the instant compositions are set forth as mole fractions.

The ZnAPSO molecular sieves of the instant invention comprise framework structures of ZnO$_2^{-2}$, AlO$_2^-$, PO$_2^+$ and SiO$_2$ tetrahedral units having an empirical chemical composition on an anhydrous basis expressed by the formula:

wherein "R" represents at least one organic templating agent present in the intracrystalline pore system; "m" represents the molar amount of "R" present per mole of (Zn$_w$Al$_x$P$_y$Si$_z$)O$_2$ and has a value of zero to about 0.3; and "w", "x", "y" and "z" represent the mole fractions of zinc, aluminum, phosphorus and silicon, respectively, present as tetrahedral oxides and each has a value of at least 0.01. The mole fractions "w", "x", "y" and "z" are generally defined being within the pentagonal compositional area defined by points A, B, C, D and E of the ternary diagram of FIG. 1. Points A, B, C, D and E of FIG. 1 have the following values for "w", "x", "y", and "z":

| Point | Mole Fraction | | |
|---|---|---|---|
| | x | y | (z + w) |
| A | 0.60 | 0.38 | 0.02 |
| B | 0.38 | 0.60 | 0.02 |
| C | 0.01 | 0.60 | 0.39 |
| D | 0.01 | 0.01 | 0.98 |
| E | 0.60 | 0.01 | 0.39 |

Figure 2:
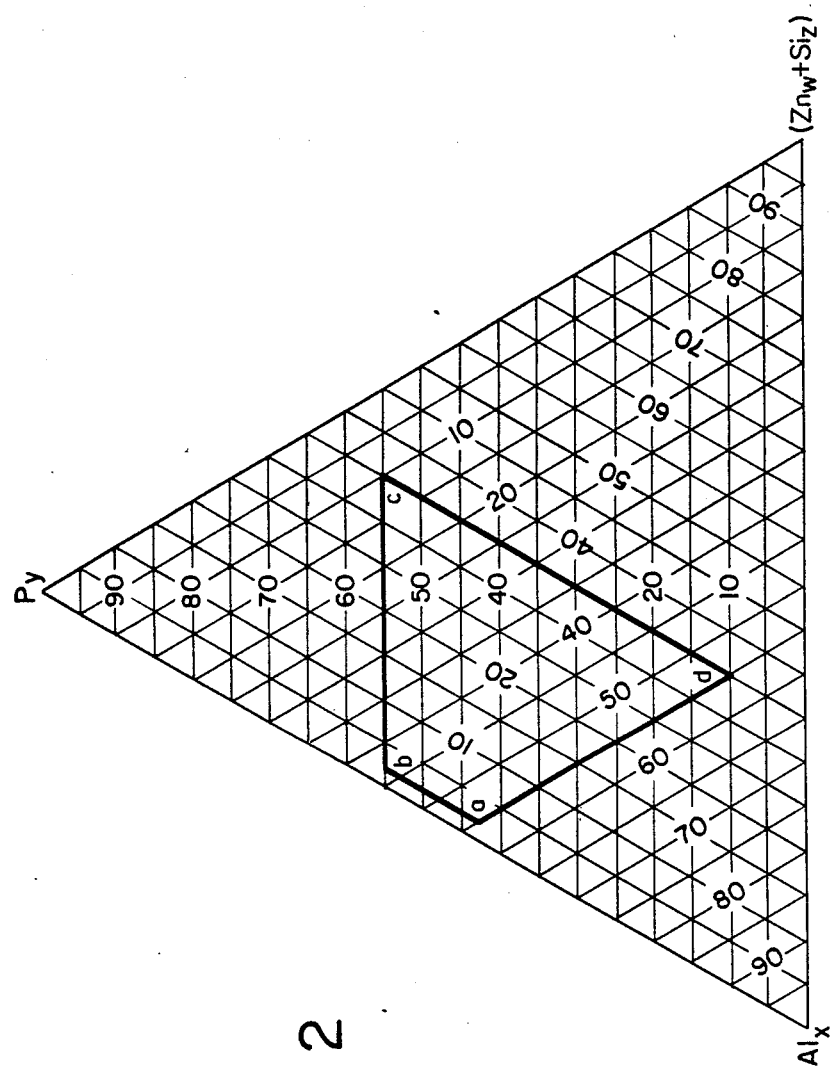
FIG. 2 is a ternary diagram wherein parameters relating to preferred compositions are set forth as mole fractions.

In the preferred subclass of ZnAPSO molecular sieves the values "w", "x", "y" and "z" in the above formular are within the tetragonal compositional area defined by points a, b, c and d of the ternary diagram which is FIG. 2 of the drawings, said points a, b, c and d representing the following values for "w", "x", "y" and "z".

| Point | Mole Fraction | | |
|---|---|---|---|
| | x | y | (z + w) |
| a | 0.55 | 0.43 | 0.02 |
| b | 0.43 | 0.55 | 0.02 |
| c | 0.10 | 0.55 | 0.35 |
| d | 0.55 | 0.10 | 0.35 |

The ZnAPSOs of this invention are useful as adsorbents, catalysts, ion-exchangers, and the like in much the same fashion as aluminosilicates have been employed heretofore, although their chemical and physical properties are not necessarily similar to those observed for aluminosilicates.

ZnAPSO compositions are generally synthesized by hydrothermal crystallization at effective process conditions from a reaction mixture containing active sources of zinc, silicon, aluminum and phosphorus, preferably an organic templating, i.e., structure-directing, agent, preferably a compound of an element or Group VA of the Periodic Table, and/or optionally an alkali or other metal. The reaction mixture is generally placed in a sealed pressure vessel, preferably lined with an inert plastic material such as polytetrafluoroethylene and heated, preferably under autogenous pressure at a temperature between 50° C. and 250° C., and preferably between 100° C. and 200° C. until crystals of the ZnAPSO product are obtained, usually a period of from several hours to several weeks. Generally the effective crystallization period is from about 2 hours to about 30 days with typical periods of from about 4 hours to about 20 days being employed to obtain ZnAPSO products. The product is recovered by any convenient method such as centrifugation or filtration.

Figure 3:
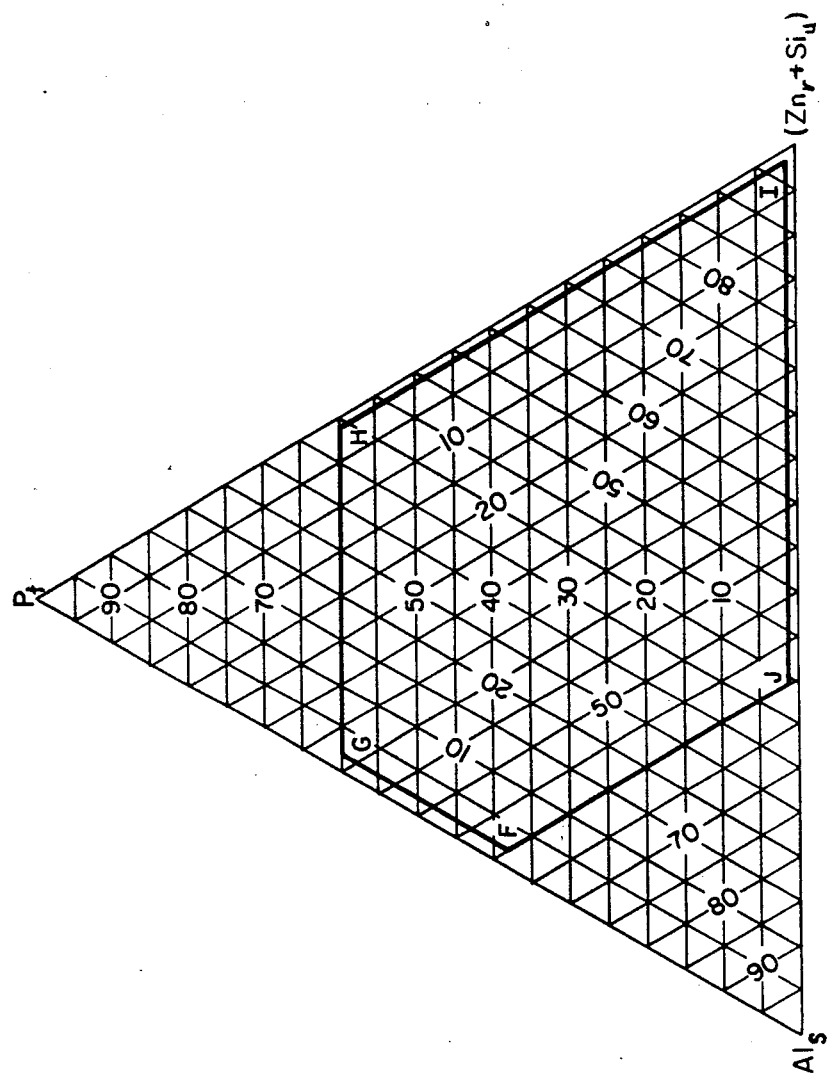
FIG. 3 is a ternary diagram wherein parameters relating to the reaction mixtures employed in the preparation of the compositions of this invention are set forth as mole fractions.

In synthesizing the ZnAPSO compositions of the instant invention, it is preferred to employ a reaction mixture composition expressed in terms of the molar ratios as follows:

$$aR:(Zn_rAl_sP_tSi_u)O_2:bH_2O$$

wherein "R" is an organic templating agent; "a" is the amount of organic templating agent "R" and has a value of from zero to about 6 and is preferably an effective amount within the range of greater than zero (0) to about 6; "b" has a value of from zero (0) to about 500, more preferably between about 2 and about 300; and "r", "s", "t" and "u" represent the mole fractions of zinc, aluminum, phosphorus and silicon, respectively, and each has a value of at least 0.01. In a preferred embodiment the reaction mixture is selected such that the mole fractions "r", "s", "t" and "u" are generally defined as being within the pentagonal compositional area defined by points F, G, H, I and J of the ternary diagram of FIG. 3. Points F, G, H, I and J of FIG. 3 have the following values for "r", "s", "t" and "u":

| Point | Mole Fraction | | |
|---|---|---|---|
| | s | t | (u + r) |
| F | 0.60 | 0.38 | 0.02 |
| G | 0.38 | 0.60 | 0.02 |
| H | 0.01 | 0.60 | 0.39 |
| I | 0.01 | 0.01 | 0.98 |
| J | 0.60 | 0.01 | 0.39 |

For reasons unknown at present, not every reaction mixture gave crystalline ZnAPSO products when reaction products were examined for ZnAPSO products by X-ray analysis. Those reaction mixtures from which crystalline ZnAPSO products were obtained are reported in the examples hereinafter as numbered examples and those reaction mixtures from which ZnAPSO products were not identified by use of X-ray analysis are reported as lettered examples.

In the foregoing expression of the reaction composition, the reactants are normalized with respect to the total of "r", "s", "t" and "u" such that $(r+s+t+u)=1.00$ mole, whereas in the examples the reaction mixtures are expressed in terms of molar oxide ratios and may be normalized to the moles of $P_2O_5$. This latter form is readily converted to the former form by routine calculations by dividing the number of moles of each component (including the template and water) by the total number of moles of zinc, aluminum, phosphorus and silicon which results in normalized mole fractions based on total moles of the aforementioned components.

In forming reaction mixture from which the instant molecular sieves are formed the organic templating agent can be any of those heretofore proposed for use in the synthesis of conventional zeolite aluminosilicates. In general these compounds contain elements of Group VA of the Periodic Table of Elements, particularly nitrogen, phosphorus, arsenic and antimony, preferably nitrogen or phosphorus and most preferably nitrogen, which compounds also contain at least one alkyl or aryl group having from 1 to 8 carbon atoms. Particularly preferred compounds for use as templating agents are the amines, quaternary phosphonium compounds and quaternary ammonium compounds, the latter two being represented generally by the formula $R_4X^+$ wherein "X" is nitrogen or phosphorus and each R is an alkyl or aryl group containing from 1 to 8 carbon atoms. Polymeric quaternary ammonium salts such as $[(C_{14}H_{32}N_2)(OH)_2]_x$ wherein "x" has a value of at least 2 are also suitably employed. The mono-, di- and tri-amines are advantageously utilized, either alone or in combination with a quaternary ammonium compound or other templating compound. Mixtures of two or more templating agents can either produce mixtures of the desired ZnAPSOs or the more strongly directing templating species may control the course of the reaction with the other templating species serving primarily to establish the pH conditions of the reaction gel. Representative templating agents include: tetramethylammonium; tetraethylammonium; tetrapropylammonium; tetrabutylammonium ions; tetrapentylammonium ions; di-n-propylamine; tripropylamine; triethylamine; triethanolamine; piperidine; cyclohexylamine; 2-methylpyridine; N,N-dimethylbenzylamine; N,N-dimethylethanolamine; choline; N,N'-dimethylpiperazine; 1,4-diazabicyclo (2,2,2) octane; N-methyldiethanolamine, N-methylethanolamine; N-methylpiperidine; 3-methylpiperidine; N-methylcyclohexylamine; 3-methylpyridine; 4-methylpyridine; quinuclidine; N,N'-dimethyl-1,4-diazabicyclo (2,2,2) octane ion; di-n-butylamine, neopentylamine; di-n-pentylamine; isopropylamine; t-butylamine; ethylenediamine; pyrrolidine; and 2-imidazolidone. Not every templating agent will direct the formation of every species of ZnAPSO, i.e., a single templating agent can, with proper manipulation of the reaction conditions, direct the formation of several ZnAPSO compositions, and a given ZnAPSO composition can be produced using several different templating agents.

The source of silicon may be silica, either as a silica sol or as fumed silica, a reactive solid amorphous precipitated silica, silica gel, alkoxides of silicon, silicic acid or alkali metal silicate and the like; such that the formation of reactive silicon in situ is provided to form $SiO_2$ tetrahedral units.

The most suitable phosphorus source yet found for the present process is phosphoric acid, but organic phosphates such as triethyl phosphate have been found satisfactory, and so also have crystalline or amorphous aluminophosphates such as the $AlPO_4$ composition of U.S. Pat. No. 4,310,440. Organo-phosphorus compounds, such as tetrabutylphosphonium bromide do not, apparently, serve as reactive sources of phosphorus, but these compounds do function as templating agents. Conventional phosphorus salts such as sodium metaphosphate, may be used, at least in part, as the phosphorus source, but are not preferred.

The preferred aluminum source is either an aluminum alkoxide, such as aluminum isoproproxide, or pseudo-boehmite. The crystalline or amorphous aluminophosphates which are a suitable source of phosphorus are, of course, also suitable sources of aluminum. Other sources of aluminum used in zeolite synthesis, such as gibbsite, sodium aluminate and aluminum trichloride, can be employed but are not preferred.

The source of zinc can be introduced into the reaction system in any form which permits the formation in situ of reactive form of zinc, i.e., reactive to form the framework tetrahedral unit $ZnO_2^{-2}$. Compounds of zinc which may be employed include oxides, hydroxides, alkoxides, nitrates, sulfates, carboxylates (e.g., acetates), organometallic zinc compounds and the like, and mixtures thereof.

While not essential to the synthesis of ZnAPSO compositions, stirring or other moderate agitation of the reaction mixture and/or seeding the reaction mixture with seed crystals of either the ZnAPSO species to be produced or a topologically similar aluminophosphate, aluminosilicate or molecular sieve composition, facilitates the crystallization procedure.

After crystallization the ZnAPSO product may be isolated and advantageously washed with water and dried in air. The as-synthesized ZnAPSO generally contains within its internal pore system at least one form of the templating agent employed in its formation. Most commonly any organic moiety derived from an organic template is present, at least in part, as a charge-balancing cation as is generally the case with as-synthesized aluminosilicate zeolites prepared from organic-containing reaction systems. It is possible, however, that some or all of the organic moiety is an occluded molecular species in a particular ZnAPSO species. As a general rule the templating agent, and hence the occluded organic species, is too large to move freely through the pore system of the ZnAPSO product and must be removed by calcining the ZnAPSO at temperatures of 200° C. to 700° C. to thermally degrade the organic species. In a few instances the pores of the ZnAPSO product are sufficiently large to permit transport of the templating agent, particularly if the latter is a small molecule, and accordingly complete or partial removal thereof can be accomplished by conventional desorption procedures such as carried out in the case of zeolites. It will be understood that the term "as-synthesized" as used herein does not include the condition of the ZnAPSO phase wherein the organic moiety occupying the intracrystalline pore system as a result of the hydrothermal crystallization process has been reduced by post-synthesis treatment such that the value of "m" in the composition formula

$$mR:(Zn_wAl_xP_ySi_z)O_2$$

has a value of less than 0.02. The other symbols of the formula are as defined hereinabove. In those preparations in which an alkoxide is employed as the source of zinc, aluminum, phosphorus or silicon, the corresponding alcohol is necessarily present in the reaction mixture since it is a hydrolysis product of the alkoxide. It has not been determined whether this alcohol participates in the syntheses process as a templating agent. For the purposes of this application, however, this alcohol is arbitrarily omitted from the class of templating agents, even if it is present in the as-synthesized ZnAPSO material.

Since the present ZnAPSO compositions are formed from $ZnO_2$, $AlO_2$, $PO_2$ and $SiO_2$ tetrahedral units which, respectively, have a net charge of $-2$, $-1$, $+1$ and 0. The matter of cation exchangeability is considerably more complicated than in the case of zeolitic molecular sieves in which, ideally, there is a stoichiometric relationship between $AlO_2^-$ tetrahedra and charge-balancing cations. In the instant compositions, an $AlO_2^-$ tetrahedron can be balanced electrically either by association with a $PO_2^+$ tetrahedron or a simple cation such as an alkali metal cation, a proton ($H^+$), a cation of zinc present in the reaction mixture, or an organic cation derived from the templating agent. Similarly an $ZnO_2^{-2}$ tetrahedron can be balanced electrically by association with $PO_2^+$ tetrahedra, a simple cation such as an alkali metal cation, a proton ($H^+$), a cation of the zinc present in the reaction mixture, organic cations derived from the templating agent, or other divalent or polyvalent metal cations introduced from an extraneous source. It has also been postulated that non-adjacent $AlO_2^-$ and $PO_2^+$ tetrahedral pairs can be balanced by $Na^+$ and $OH^-$ respectively [Flanigen and Grose. Molecular Sieve Zeolites-I, ACS, Washington, D.C. (1971)]

The ZnAPSO compositions of the present invention exhibit cation-exchange capacity when analyzed using ion-exchange techniques heretofore employed with zeolitic aluminosilicates and have uniform pore diameters which are inherent in the lattice structure of each species and which are at least about 3 Å in diameter. Ion exchange of ZnAPSO compositions is ordinarily possible only after the organic moiety present as a result of synthesis has been removed from the pore system. Dehydration to remove water present in the as-synthesized ZnAPSO compositions can usually be accomplished, to some degree at least, in the usual manner without removal of the organic moiety, but the absence of the organic species greatly facilitates adsorption and desorption procedures. The ZnAPSO materials have various degrees of hydrothermal and thermal stability, some being quite remarkable in this regard, and function well as molecular sieve adsorbents and hydrocarbon conversion catalysts or catalyst bases.

In each example a stainless steel reaction vessel was utilized and was lined with the inert plastic material, polytetrafluoroethylene, to avoid contamination of the reaction mixture. In general, the final reaction mixture from which each ZnAPSO composition is crystallized is prepared by forming mixtures of less than all of the reagents and thereafter incorporating into these mixtures additional reagents either singly or in the form of other intermediate mixtures of two or more reagents. In some instances the reagents admixed retain their identity in the intermediate mixture and in other cases some or all of the reagents are involved in chemical reactions to produce new reagents. The term "mixture" is applied in both cases. Further, unless otherwise specified, each intermediate mixture as well as the final reaction mixture was stirred until substantially homogeneous.

X-ray analysis of reaction products are obtained by X-ray analysis, using standard X-ray powder diffraction techniques. The radiation source is a high-intensity, copper target, X-ray tube operated at 50 Kv and 40 ma. The diffraction pattern from the copper K-alpha radiation and graphite monochromator is suitably recorded by an X-ray spectrometer scintillation counter, pulse height analyzer and strip chart recorder. Flat compressed powder samples are scanned at 2° (2 theta) per minute, using a two second time constant. Interplanar spacings (d) in Angstrom units are obtained from the position of the diffraction peaks expressed as $2\theta$ where $\theta$ is the Bragg angle as observed on the strip chart. Intensities are determined from the heights of diffraction peaks after subtracting background, "$I_o$" being the intensity of the strongest line or peak, and "I" being the intensity of each of the other peaks. Alternatively, the X-ray patterns are obtained from the copper K-alpha radiation by use of computer based techniques using Siemens D-500 X-ray powder diffractometers, Siemens Type K-805 X-ray sources, available from Siemens Corporation, Cherry Hill, N.J., with appropriate computer interface.

As will be understood by those skilled in the art the determination of the parameter 2 theta is subject to both human and mechanical error, which in combination, can impose an uncertainty of about ±0.4° on each reported value of 2 theta. This uncertainty is, of course, also manifested in the reported values of the d-spacings, which are calculated from the 2 theta values. This imprecision is general throughout the art and is not sufficient to preclude the differentiation of the present crystalline materials from each other and from the compositions of the prior art. In some of the X-ray patterns reported, the relative intensities of the d-spacings are indicated by the notations vs, s, m, w and vw which represent very strong, strong, medium, weak and very weak respectively.

In certain instances the purity of a synthesized product may be assessed with reference to its X-ray powder diffraction pattern. Thus, for example, if a sample is stated to be pure, it is intended only that the X-ray pattern of the sample is free of lines attributable to crystalline impurities, not that there are no amorphous materials present.

The molecular sieves of the instant invention may be characterized by their x-ray powder diffraction patterns and such may have one of the x-ray patterns set forth in the following Tables A through N, wherein said x-ray patterns are for both the as-synthesized and calcined forms unless otherwise noted:

TABLE A (ZnAPSO-5)

| 2θ | d(Å) | Relative Intensity |
|---|---|---|
| 7.2–7.4 | 12.28–11.91 | vs |
| 19.4–19.8 | 4.58–4.48 | m |
| 21.0–21.2 | 4.23–4.19 | m |
| 22.3–22.5 | 3.971–3.952 | m–s |
| 25.7–26.0 | 3.466–3.427 | w–m |

TABLE B (ZnAPSO-11)

| 2θ | d(Å) | Relative Intensity |
|---|---|---|
| 9.35–9.45 | 9.44–9.35 | m |
| 13.15–13.35 | 6.67–6.63 | m |
| 21.1–21.25 | 4.21–4.19 | s–vs |
| 22.75–22.85 | 3.911–3.896 | s–vs |
| 23.15–23.3 | 3.839–3.819 | w–m |
| 26.8–26.9 | 3.327–3.313 | w–m |

TABLE C (ZnAPSO-20)

| 2θ | d(Å) | Relative Intensity |
|---|---|---|
| 13.85–14.0 | 6.39–6.33 | m |
| 19.65–19.8 | 4.52–4.48 | m |
| 24.15–24.3 | 3.685–3.663 | vs |
| 28.0–28.15 | 3.187–3.170 | w |
| 31.35–31.5 | 2.853–2.840 | w |
| 34.5–34.65 | 2.600–2.589 | w–m |

TABLE D (ZnAPSO-31)

| 2θ | d(Å) | Relative Intensity |
|---|---|---|
| 8.4–8.5 | 10.53–10.40 | m |
| 20.2–20.3 | 4.40–4.37 | m |
| 21.3 | 4.171 | w |
| 22.0 | 4.036 | m |
| 22.5–22.6 | 3.952–3.934 | vs |
| 31.6–31.75 | 2.831–2.820 | w–m |

TABLE E (ZnAPSO-34)

| 2θ | d(Å) | Relative Intensity |
|---|---|---|
| 9.4–9.8 | 9.41–9.03 | m–vs |
| 12.7–13.2 | 6.97–6.71 | w–m |
| 15.8–16.2 | 5.61–5.47 | w–m |
| 20.5–20.9 | 4.33–4.25 | m–vs |
| 25.0–25.3 | 3.562–3.520 | vw–m |
| 30.5–30.9 | 2.931–2.894 | w–m |

TABLE F (ZnAPSO-35)

| 2θ | d(Å) | Relative Intensity |
|---|---|---|
| 10.8–11.0 | 8.19–8.04 | m–vs |
| 13.30–13.5 | 6.66–6.56 | m–vs |
| 17.2–17.45 | 5.16–5.08 | m |
| 20.95–21.2 | 4.24–4.19 | m |
| 21.9–22.15 | 4.06–4.01 | m–vs |
| 32.0–32.5 | 2.797–2.755 | m |

TABLE G (ZnAPSO-36)

| 2θ | d(Å) | Relative Intensity |
|---|---|---|
| 7.45–8.0 | 11.14–11.04 | vs |
| 16.45–16.5 | 5.38–5.36 | w–m |
| 19.1–19.2 | 4.65–4.62 | w–m |
| 20.8–20.9 | 4.28–4.25 | w–m |
| 21.75–21.8 | 4.09–4.08 | w |
| 22.05–22.15 | 4.027–4.017 | w |

TABLE H (ZnAPSO-39)

| 2θ | d(Å) | Relative Intensity |
|---|---|---|
| 9.35–9.45 | 9.46–9.36 | m |
| 13.15–13.35 | 6.73–6.63 | m |
| 18.3–18.4 | 4.85–4.82 | w–m |
| 21.1–21.2 | 4.21–4.19 | s–vs |
| 22.75–22.85 | 3.909–3.892 | s–vs |
| 26.8–26.9 | 3.389–3.314 | w–m |

TABLE J (ZnAPSO-43)

| 2θ | d(Å) | Relative Intensity |
|---|---|---|
| 12.3–12.45 | 7.20–7.11 | m–vs |
| 16.8–16.95 | 5.28–5.23 | vw–w |
| 21.7–21.85 | 4.095–4.068 | vw–m |
| 26.95–27.1 | 3.308–3.291 | s–vs |
| 32.4–32.55 | 2.763–2.751 | w–m |

TABLE K (ZnAPSO-44)

| 2θ | d(Å) | Relative Intensity |
|---|---|---|
| 9.4–9.55 | 9.41–9.26 | vs |
| 12.9–13.05 | 6.86–6.78 | vw–m |
| 20.65–20.8 | 4.30–4.27 | m |
| 21.4–21.8 | 4.15–4.08 | w–m |

TABLE K-continued

| 2θ | (ZnAPSO-44) d(Å) | Relative Intensity |
|---|---|---|
| 24.3–25.15 | 3.663–3.541 | m |
| 30.75–30.95 | 2.908–2.889 | m |

TABLE L

| 2θ | (ZnAPSO-46) d(Å) | Relative Intensity |
|---|---|---|
| 7.6–7.75 | 11.63–11.42 | vs |
| 13.1–13.35 | 6.76–6.63 | w–m |
| 21.5–21.6 | 4.13–4.12 | w–m |
| 22.6–22.85 | 3.934–3.896 | m |
| 26.75–27.0 | 3.333–3.302 | w |

TABLE M

| 2θ | (ZnAPSO-47) d(Å) | Relative Intensity |
|---|---|---|
| 9.45–9.65 | 9.35–9.17 | vs |
| 12.85–13.05 | 6.89–6.78 | w–m |
| 15.95–16.2 | 5.55–5.46 | w–m |
| 20.55–20.85 | 4.31–4.26 | m–vs |
| 25.9–26.2 | 3.439–3.399 | w–m |
| 30.55–31.0 | 2.925–2.885 | w–m |

The following examples are provided to further illustrate the invention and are not intended to be limiting thereof:

PREPARATIVE REAGENTS

In the following examples the ZnAPSO compositions were prepared using numerous reagents. The reagents emplyed and abbreviations employed herein, if any, for such reagents are as follows:

(a) Alipro: aluminum isopropoxide;
(b) LUDOX-LS: LUDOX-LS is the trade name of DuPont for an aqueous solution of 30 weight percent $SiO_2$ and 0.1 weight percent $Na_2O$;
(c) CATAPAL: Trademark of Condea Corporation for hydrated pseudoboehmite.
(d) $H_3PO_4$: 85 weight percent aqueous phosphoric acid;
(e) ZnAc: Zinc Acetate, $Zn(C_2H_3O_2)_2 \cdot 4H_2O$;
(f) TEAOH: 40 weight percent aqueous solution of tetraethylammonium hydroxide;
(g) TBAOH: 40 weight percent aqueous solution of tetrabutylammonium hydroxide;
(h) TMAOH: Tetramethylammonium hydroxide pentahydrate, $(CH_3)_4NOH \cdot 5H_2O$;
(i) TPAOH: 40 weight percent aqueous solution of tetrapropylammonium hydroxide, $(C_3H_7)_4NOH$;
(j) $Pr_2NH$: di-n-propylamine, $(C_3H_7)_2NH$;
(k) $Pr_3N$: Tri-n-propylamine, $(C_3H_7)_3N$;
(l) Quin: Quinuclidine, $(C_7H_{13}N)$;
(m) C-hex: cyclohexylamine; and
(n) DEEA: diethylethanolamine, $(C_2H_5)_2NC_2H_5OH$.

PREPARATIVE PROCEDURE

The ZnAPSO compositions were prepared by preparing reaction mixtures having a molar composition expressed as:

$$eR:fZnO:gAl_2O_3:hP_2O_5:iSiO_2:jH_2O$$

wherein e, f, g, h, i and j represent the moles of template R, zinc (expressed as the oxide), $Al_2O_3$, $P_2O_5$ ($H_3PO_4$ expressed as $P_2O_5$), $SiO_2$ and $H_2O$, respectively. The values for e, f, g, h, i and j were as set forth in the hereinafter discussed preparative examples where "j" was 50 in each example, and "e" was 1.0.

The reaction mixtures were prepared by forming a starting reaction mixture comprising the $H_3PO_4$ and a portion of the water. This mixture was stirred and the aluminum source added. The resulting mixture was blended until a homogeneous mixture was observed. The LUDOX LS was then added to the resulting mixture and the new mixture blended until a homogeneous mixture was observed. The zinc source (zinc acetate) was dissolved in the remaining water and combined with the first mixture. The combined mixture was blended until a homogeneous mixture was observed. The organic templating agent was added to this mixture and blended for about two to four minutes until a homogeneous mixture was observed. The resulting mixture (final reaction mixture) was placed in a lined (polytetrafluoroethylene) stainless steel pressure vessel and digested at an effective temperature for an effective time. All digestions were carried out at the autogeneous pressure. The products were removed from the reaction vessel cooled and evaluated as set forth hereinafter.

EXAMPLES 1 TO 41

ZnAPSO molecular sieves were prepared according to the above described procedure and the ZnAPSO products determined by x-ray analysis. The results of preparative examples 1 to 41 are set forth in Tables I and II. The reactive zinc source was zinc acetate. The reactive aluminum source was Al-ipro. The reactive phosphorus source was $H_3PO_4$. the reactive silicon source was LUDOX-LS. The organic templating agents are set forth in Tables I and II.

TABLE I

| Example[2] | Template | f | g | h | i | Temp (°C.) | Time (hrs) | ZnAPSO Product(s)[1] |
|---|---|---|---|---|---|---|---|---|
| 1 | $Pr_3N$ | 0.1 | 1.0 | 1.0 | 0.6 | 150 | 42 | ZnAPSO-36; ZnAPSO-5 |
| 2 | $Pr_3N$ | 0.1 | 1.0 | 1.0 | 0.6 | 150 | 183 | ZnAPSO-36; ZnAPSO-5 |
| 3 | $Pr_3N$ | 0.1 | 1.0 | 1.0 | 0.6 | 200 | 42 | ZnAPSO-5; ZnAPSO-36 |
| 4 | $Pr_3N$ | 0.1 | 1.0 | 1.0 | 0.6 | 200 | 183 | ZnAPSO-5; ZnAPSO-36 |
| 5 | $Pr_3N$ | 0.2 | 0.9 | 0.9 | 0.2 | 150 | 48 | ZnAPSO-5; ZnAPSO-36 |
| 6 | TPAOH | 0.2 | 0.9 | 0.7 | 0.6 | 200 | 165 | ZnAPSO-5; |
| 7 | TPAOH | 0.2 | 0.9 | 0.7 | 0.6 | 200 | 165 | ZnAPSO-5 |
| 8 | $Pr_2N$ | 0.1 | 1.0 | 1.0 | 0.6 | 150 | 42 | ZnAPSO-46; ZnAPSO-39; ZnAPSO-11 |
| 9 | $Pr_2NH$ | 0.1 | 1.0 | 1.0 | 0.6 | 150 | 183 | ZnAPSO-39; ZnAPSO-11; ZnAPSO-46 |
| 10 | $Pr_2NH$ | 0.1 | 1.0 | 1.0 | 0.6 | 200 | 42 | ZnAPSO-11; ZnAPSO-46; ZnAPSO-39 |
| 11 | $Pr_2NH$ | 0.1 | 1.0 | 1.0 | 0.6 | 200 | 183 | ZnAPSO-11; ZNAPSO-39; ZnAPSO-46 |
| 12 | $Pr_2NH$ | 0.2 | 0.9 | 0.7 | 0.6 | 150 | 41 | ZnAPSO-46; ZnAPSO-31; |

TABLE I-continued

| Example[2] | Template | f | g | h | i | Temp (°C.) | Time (hrs) | ZnAPSO Product(s)[1] |
|---|---|---|---|---|---|---|---|---|
| 13 | Pr₂NH | 0.2 | 0.9 | 0.7 | 0.6 | 150 | 145 | ZnAPSO-31; ZnAPSO-46 |
| 14 | Pr₂NH | 0.2 | 0.9 | 0.7 | 0.6 | 200 | 41 | ZnAPSO-31 |
| 15 | Pr₂NH | 0.2 | 0.9 | 0.7 | 0.6 | 200 | 145 | ZnAPSO-31 |

[1]Major species as identified by x-ray powder diffraction pattern of product, except that when two or more species were identified the species are listed in the order of their predominance in the product.
[2]AlPO₄-31 (U.S. Pat. No. 4,310,440) seed employed in examples 12 to 15.

TABLE II

| Example | Template | f | g | h | i | Temp (°C.) | Time (hrs) | ZnAPSO Product(s)[1] |
|---|---|---|---|---|---|---|---|---|
| 16 | TEAOH | 0.1 | 1.0 | 1.0 | 0.6 | 100 | 134 | ZnAPSO-34 |
| 17 | TEAOH | 0.1 | 1.0 | 1.0 | 0.6 | 100 | 251 | ZnAPSO-34 |
| 18 | TEAOH | 0.1 | 1.0 | 1.0 | 0.6 | 150 | 134 | ZnAPSO-5; ZNAPSO-34 |
| 19 | TEAOH | 0.1 | 1.0 | 1.0 | 0.6 | 150 | 251 | ZnAPSO-34; ZnAPSO-5 |
| 20 | TEAOH | 0.1 | 1.0 | 1.0 | 0.6 | 200 | 134 | ZnAPSO-5; ZnAPSO-34 |
| 21 | TEAOH | 0.1 | 1.0 | 1.0 | 0.6 | 200 | 251 | ZnAPSO-34; ZnAPSO-5 |
| 22 | TEAOH | 0.1 | 0.95 | 0.7 | 0.6 | 100 | 17 | ZnAPSO-34 |
| 23 | TEAOH | 0.1 | 0.95 | 0.7 | 0.6 | 100 | 66 | ZnAPSO-34 |
| 24 | TEAOH | 0.1 | 0.95 | 0.7 | 0.6 | 100 | 166 | ZnAPSO-34 |
| 25 | TEAOH | 0.1 | 0.95 | 0.7 | 0.6 | 100 | 66 | ZnAPSO-34 |
| 26 | TMAOH | 0.2 | 0.9 | 0.7 | 0.6 | 150 | 46 | ZnAPSO-20; ZnAPSO-43 |
| 27 | TMAOH | 0.2 | 0.9 | 0.7 | 0.6 | 150 | 165 | ZnAPSO-20; ZnAPSO-43 |
| 28 | TMAOH | 0.2 | 0.9 | 0.7 | 0.6 | 200 | 46 | ZnAPSO-20; ZnAPSO-43 |
| 29 | TMAOH | 0.2 | 0.9 | 0.7 | 0.6 | 200 | 165 | ZnAPSO-20; ZnAPSO-43 |
| 30 | QUIN | 0.2 | 0.9 | 0.7 | 0.6 | 150 | 40 | ZnAPSO-35 |
| 31 | Quin | 0.2 | 0.9 | 0.7 | 0.6 | 150 | 158 | ZnAPSO-35 |
| 32 | Quin | 0.2 | 0.9 | 0.7 | 0.6 | 200 | 40 | ZnAPSO-35 |
| 33 | Quin | 0.2 | 0.9 | 0.7 | 0.6 | 200 | 158 | ZnAPSO-35 |
| 34 | C-hex | 0.2 | 0.9 | 0.7 | 0.6 | 150 | 40 | ZnAPSO-44 |
| 35 | C-hex | 0.2 | 0.9 | 0.7 | 0.6 | 150 | 158 | ZnAPSO-44 |
| 36 | C-hex | 0.2 | 0.9 | 0.7 | 0.6 | 200 | 40 | ZnAPSO-44; ZnAPSO-5 |
| 37 | C-hex | 0.2 | 0.9 | 0.7 | 0.6 | 200 | 158 | ZnAPSO-44; ZnAPSO-5 |
| 38 | DEEA | 0.2 | 0.9 | 0.7 | 0.6 | 150 | 40 | ZnAPSO-47; ZnAPSO-5 |
| 39 | DEEA | 0.2 | 0.9 | 0.7 | 0.6 | 150 | 158 | ZnAPSO-47; ZnAPSO-5 |
| 40 | DEEA | 0.2 | 0.9 | 0.7 | 0.6 | 200 | 40 | ZnAPSO-47; ZnAPSO-5 |
| 41 | DEEA | 0.2 | 0.9 | 0.7 | 0.6 | 200 | 158 | ZnAPSO-47 |

[1]Major species as identified by x-ray powder diffraction pattern of product, except that when two or more species were identified the species are listed in the order of their predominance in the product.

EXAMPLE 42

Samples of the products of examples 4, 17, 24, 33, 35 and 39 were subjected to chemical analysis. The chemical analysis for each product is given hereinafter with the example in which the ZnAPSO was prepared being given in parenthesis after the designation of the ZnAPSO species.

(a) The chemical analysis for ZnAPSO-5 (Example 4) was:

| Component | Weight Percent |
|---|---|
| Al₂O₃ | 31.3 |
| P₂O₅ | 45.7 |
| ZnO | 2.8 |
| SiO₂ | 5.7 |
| Carbon | 5.5 |
| LOI* | 12.8 |

*LOI = Loss on Ignition

The above chemical analysis gives an overall product composition in molar oxide ratios (anhydrous basis) of: 0.17 R; 0.11 ZnO; 1.0 Al₂O₃; 1.05 P₂O₅; 0.31 SiO₂; and a formula (anhydrous basis) of:

$$0.04\ R\ (Zn_{0.03}Al_{0.44}O_{0.47}Si_{0.07})O_2$$

(b) The chemical analysis for ZnAPSO-34 (Example 17) was:

| Component | Weight Percent |
|---|---|
| Al₂O₃ | 32.3 |
| P₂O₅ | 35.3 |
| ZnO | 2.8 |
| SiO₂ | 1.6 |
| Carbon | 5.0 |
| LOI* | 26.7 |

*LOI = Loss on Ignition

The above chemical analysis gives an overall product composition in molar oxide ratios (anhydrous basis) of: 0.16 R; 0.11 ZnO; 1.0 Al₂O₃; 0.79 P₂O₅: 0.08 SiO₂; and a formula (anhydrous basis) of:

$$0.04\ R\ (Zn_{0.03}Al_{0.54}P_{0.41}Si_{0.02})O_2$$

(c) The chemical analysis for ZnAPSO-34 (Example 24) was:

| Component | Weight Percent |
|---|---|
| Al₂O₃ | 36.2 |
| P₂O₅ | 30.3 |
| ZnO | 3.8 |
| SiO₂ | 3.7 |
| Carbon | 5.2 |
| LOI* | 24.0 |

*LOI = Loss on Ignition

The above chemical analysis gives an overall product composition in molar oxide ratios of 0.15 R; 0.13 ZnO;

1.0 Al$_2$O$_3$; 0.60 P$_2$O$_5$: 0.07 SiO$_2$; and a formula (anhydrous basis) of:

0.04 R (Zn$_{0.04}$Al$_{0.57}$P$_{0.34}$Si$_{0.05}$)O$_2$ (d) The chemical analysis of ZnAPSO-35 (Example 33) was:

| Component | Weight Percent |
|---|---|
| Al$_2$O$_3$ | 30.4 |
| P$_2$O$_5$ | 33.2 |
| ZnO | 5.6 |
| SiO$_2$ | 7.6 |
| Carbon | 10.1 |
| LOI* | 22.1 |

*LOI = Loss on Ignition

The above chemical analysis gives an overall product composition in molar oxide ratios of: 0.40 R; 0.23 ZnO; 1.0 Al$_2$O$_3$; 0.78 P$_2$O$_5$; 0.42 SiO$_2$; and a formula (anhydrous basis) of:

0.12 R (Zn$_{0.06}$Al$_{0.47}$P$_{0.37}$Si$_{0.10}$)O$_2$ (e) The chemical analysis for ZnAPSO-44 (Example 35) was:

| Component | Weight Percent |
|---|---|
| Al$_2$O$_3$ | 27.5 |
| P$_2$O$_5$ | 31.1 |
| ZnO | 4.8 |
| SiO$_2$ | 10.6 |
| Carbon | 11.7 |
| LOI* | 25.1 |

*LOI = Loss on Ignition

The above chemical analysis gives an overall product composition in molar oxide ratios of: 0.60 R; 0.22 ZnO; 1.0 Al$_2$O$_3$; 0.81 P$_2$O$_5$; 0.65 SiO$_2$; and a formula (anhydrous basis) of:

0.13 R (Zn$_{0.05}$Al$_{0.44}$P$_{0.36}$Si$_{0.15}$)O$_2$ (f) The chemical analysis of ZnAPSO-47 (Example 39) was:

| Component | Weight Percent |
|---|---|
| Al$_2$O$_3$ | 30.4 |
| P$_2$O$_5$ | 32.6 |
| ZnO | 5.3 |
| SiO$_2$ | 6.5 |
| Carbon | 7.7 |
| LOI* | 23.4 |

*LOI = Loss on Ignition

The above chemical analysis gives an overall product composition in molar oxide ratios of: 0.35 R; 0.22 ZnO; 1.0 Al$_2$O$_3$; 0.77 P$_2$O$_5$; 0.36 SiO$_2$; and a formula (anhydrous basis) of:

0.09 R (Zn$_{0.05}$Al$_{0.49}$P$_{0.37}$Si$_{0.09}$)O$_2$

EXAMPLE 43

EDAX (energy dispersive analysis by x-ray) microprobe analysis in conjunction with SEM (scanning electron microscope was carried out on clear crystals from the products of examples 4, 24, 33, 35 and 39. Analysis of crystals having a morphology characteristic of the ZnAPSO products gave the following analysis based on relative peak heights:

| Average of Spot Probes | |
|---|---|
| (a) ZnAPSO-5 (Example 4): | |
| Zn | 1 |
| Al | 44 |
| P | 50 |
| Si | 5 |
| (b) ZnAPSO-34 (Example 24): | |
| Zn | 3 |
| Al | 45 |
| P | 46 |
| Si | 6 |
| (c) ZnAPSO-35 (Example 33): | |
| Zn | 5 |
| Al | 43 |
| P | 46 |
| Si | 6 |
| (d) ZnAPSO-36 (Example 4): | |
| Zn | 4 |
| Al | 42 |
| P | 50 |
| Si | 4 |
| (e) ZnAPSO-44 (Example 35): | |
| Zn | 2 |
| Al | 43 |
| P | 39 |
| Si | 16 |
| (f) ZnAPSO-47 (Example 39): | |
| Zn | 5 |
| Al | 42 |
| P | 44 |
| Si | 9 |

EXAMPLE 44

Samples of the ZnAPSO products of examples 4, 27, 33, 35 and 39 were for adsorption capacities evaluated in the as-synthesized form or were calcined in air or nitrogen, to remove at least part of the organic templating agent, as hereinafter set forth. The adsorption capacities of each calcined sample were measured using a standard McBain - Bakr gravimetric adsorption apparatus. The samples were activated in a vacuum at 350° C. prior to measurment. The McBain-Bakr data for the aformentioned calcing ZnAPSO products were:

| (a) ZnAPSO-5 (Example 4): | | | | |
|---|---|---|---|---|
| Adsorbate | Kinetic Diameter, Å | Pressure (Torr) | Temp (°C.) | Wt. % Adsorbed* |
| O$_2$ | 3.46 | 99 | −183 | 11.0 |
| O$_2$ | 3.46 | 749 | −183 | 14.9 |
| neopentane | 6.2 | 100 | 23.4 | 3.5 |
| cyclohexane | 6.0 | 57 | 23.4 | 7.4 |
| H$_2$O | 2.65 | 4.6 | 23.2 | 13.5 |
| H$_2$O | 2.65 | 16.8 | 23.5 | 17.5 |

*calcined in air at 500° C. for 0.75 hours and at 600° C. for 1.25 hours prior to activation.

The above data demonstrate that the pore size of the calcined product is greater than 6.2Å.

| (b) ZnAPSO-34 (Example 27): | | | | |
|---|---|---|---|---|
| Adsorbate | Kinetic Diameter, Å | Pressure (Torr) | Temp (°C.) | Wt. % Adsorbed* |
| O$_2$ | 3.46 | 99 | −183 | 14.5 |
| O$_2$ | 3.46 | 725 | −183 | 25.8 |
| isobutane | 5.0 | 100 | 22.8 | 0.8 |
| n-hexane | 4.3 | 98 | 23.3 | 13.3 |
| H$_2$O | 2.65 | 4.6 | 23.1 | 19.9 |

-continued

(b) ZnAPSO-34 (Example 27):

| Adsorbate | Kinetic Diameter, Å | Pressure (Torr) | Temp (°C.) | Wt. % Adsorbed* |
|---|---|---|---|---|
| $H_2O$ | 2.65 | 17.8 | 23.1 | 30.1 |

*calcined in air at 500° C. for 2 hours prior to activation

The above data demonstrate that the pore size of the calcined product is about 4.3Å.

(c) ZnAPSO-35 (Example 33):

| Adsorbate | Kinetic Diameter, Å | Pressure (Torr) | Temp (°C.) | Wt. % Adsorbed* |
|---|---|---|---|---|
| $O_2$ | 3.46 | 99 | −183 | 10.2 |
| $O_2$ | 3.46 | 725 | −183 | 19.1 |
| n-hexane | 4.3 | 98 | 23.3 | 8.6 |
| isobutane | 5.0 | 100 | 22.8 | 0.8 |
| $H_2O$ | 2.65 | 4.6 | 23.1 | 17.2 |
| $H_2O$ | 2.65 | 17.8 | 23.1 | 26.3 |

*calcined in air at 500° C. for 1.75 hours prior to activation

The above data demonstrate that the pore size of the calcined product is about 4.3Å.

(d) ZnAPSO-44 (Example 35):

| Adsorbate | Kinetic Diameter, Å | Pressure (Torr) | Temp (°C.) | Wt. % Adsorbed* |
|---|---|---|---|---|
| $O_2$ | 3.46 | 99 | −183 | 10.3 |
| $O_2$ | 3.46 | 745 | −183 | 19.8 |
| n-hexane | 4.3 | 98 | 23.3 | 9.7 |
| isobutane | 5.0 | 100 | 22.8 | 0.8 |
| $H_2O$ | 2.65 | 4.6 | 23.1 | 14.0 |
| $H_2O$ | 2.65 | 17.8 | 23.1 | 24.0 |

*calcined in air at 500° C. for 67 hours prior to activation

The above data demonstrate that the pore size of the calcined product is about 4.3Å.

(e) ZnAPSO-47 (Example 39):

| Adsorbate | Kinetic Diameter, Å | Pressure (Torr) | Temp (°C.) | Wt. % Adsorbed* |
|---|---|---|---|---|
| $O_2$ | 3.46 | 99 | −183 | 13.9 |
| $O_2$ | 3.46 | 725 | −183 | 23.0 |
| isobutane | 5.0 | 100 | 23.8 | 0.7 |
| n-hexane | 4.3 | 98 | 23.3 | 7.8 |
| $H_2O$ | 2.65 | 4.6 | 23.1 | 18.8 |
| $H_2O$ | 2.65 | 17.8 | 23.1 | 27.0 |

*calcined in air at 500° C. for 1.75 hours prior to activation

The above data demonstrate that the pore size of the calcined product is about 4.3Å.

EXAMPLE 45

(a) ZnAPSO-5, as prepared in example 4, was subjected to x-ray analysis. ZnAPSO-5 was determined to have a characteristic x-ray powder diffraction pattern which contains at least the d-spacings set forth below:

| 2θ | d, (Å) | 100 × I/Io |
|---|---|---|
| 7.4 | 11.91 | 100 |
| 7.9** | 11.17 | 29 |
| 12.85 | 6.88 | 10 |
| 13.5* | 6.56 | 1 |
| 14.85 | 5.96 | 19 |
| 15.85** | 5.60 | 3 |
| 16.45** | 5.39 | 8 |
| 19.1** | 4.65 | 9 |
| 19.7 | 4.51 | 38 |
| 20.3** | 4.38 | 4 |
| 20.8** | 4.27 | 10 |
| 21.05 | 4.22 | 30 |
| 21.5** | 4.14 | 5 |
| 21.65** | 4.10 | 5 |
| 22.4 | 3.973 | 73 |
| 22.95* | 3.876 | 3 |
| 23.85** | 3.730 | 1 |
| 24.75 | 3.596 | 2 |
| 25.9 | 3.442 | 25 |
| 27.2** | 3.279 | 4 |
| 27.75** | 3.212 | 1 |
| 28.3** | 3.154 | 2 |
| 29.0 | 3.078 | 15 |
| 29.95 | 2.981 | 15 |
| 30.35** | 2.947 | 2 |
| 32.0** | 2.798 | 3 |
| 33.6 | 2.666 | 4 |
| 34.45 | 2.602 | 12 |
| 34.8** | 2.577 | 4 |
| 35.45** | 2.532 | 2 |
| 35.9 | 2.501 | 1 |
| 36.95 | 2.434 | 3 |
| 37.7 | 2.386 | 7 |
| 41.45* | 2.177 | 2 |
| 42.2 | 2.141 | 3 |
| 42.8 | 2.112 | 1 |
| 43.4 | 2.085 | 1 |
| 45.0 | 2.013 | 1 |
| 47.6 | 1.910 | 4 |
| 51.4 | 1.778 | 2 |
| 51.95 | 1.760 | 1 |
| 55.6* | 1.654 | 2 |

*peak may contain impurity
**impurity peak (b) A portion of the as-synthesized ZnAPSO-5 of part (a) was calcined in air at 500° C. for about 0.75 hours and then in air at 600° C. for about 1.5 hours. The calcined product was characterized by the x-ray powder diffraction pattern below:

| 2θ | d, (Å) | 100 × I/Io |
|---|---|---|
| 7.45 | 11.91 | 100 |
| 7.85* | 11.23 | 21 |
| 8.2* | 10.79 | 7 |
| 12.9 | 6.87 | 20 |
| 13.45* | 6.57 | 3 |
| 14.9 | 5.95 | 6 |
| 16.5* | 5.37 | 5 |
| 19.35* | 4.58 | 5 |
| 19.75 | 4.49 | 24 |
| 20.3 | 4.38 | 10 |
| 20.7 | 4.29 | 4 |
| 21.1 | 4.21 | 28 |
| 21.4 | 4.14 | 11 |
| 22.4 | 3.962 | 69 |
| 22.75* | 3.907 | 5 |
| 24.85 | 3.584 | 2 |
| 26.0 | 3.430 | 24 |
| 27.25* | 3.275 | 4 |
| 27.45* | 3.252 | 2 |
| 27.8* | 3.207 | 2 |
| 28.15* | 3.168 | 3 |
| 28.35* | 3.146 | 2 |
| 29.1 | 3.068 | 16 |
| 30.1 | 2.970 | 14 |
| 33.7 | 2.658 | 3 |
| 34.6 | 2.592 | 13 |
| 35.45* | 2.532 | 4 |
| 37.05 | 2.427 | 3 |
| 37.85 | 2.378 | 6 |
| 42.4 | 2.132 | 2 |
| 47.8 | 1.903 | 2 |
| 51.5 | 1.774 | 3 |
| 55.8 | 1.647 | 1 |

*Impurity Peak (c) The ZnAPSO-5 compositions are generally characterized by the data of Table III below.

TABLE III

| 2θ | d (Å) | Relative Intensity |
|---|---|---|
| 7.2–7.4 | 12.28–11.91 | vs |
| 19.4–19.8 | 4.58–4.48 | m |
| 21.0–21.2 | 4.23–4.19 | m |
| 22.3–22.5 | 3.971–3.952 | m–s |
| 25.7–26.0 | 3.466–3.427 | w–m |

(d) The ZnAPSO-5 compositions for which x-ray powder diffraction data have been obtained to date have patterns which are characterized by the x-ray powder diffraction pattern shown in Table IV, below.

TABLE IV

| 2θ | d, (Å) | 100 × I/Io |
|---|---|---|
| 7.2–7.4 | 12.28–11.91 | 100 |
| 12.61–13.0 | 7.03–6.81 | 8–21 |
| 14.6–14.9 | 6.07–5.95 | 9–20 |
| 19.4–19.8 | 4.58–4.48 | 24–38 |
| 21.0–21.2 | 4.23–4.19 | 20–35 |
| 22.3–22.5 | 3.971–3.952 | 47–82 |
| 24.7–24.9 | 3.604–3.576 | 1–2 |
| 25.7–26.0 | 3.466–3.427 | 18–27 |
| 28.9–29.1 | 3.089–3.069 | 10–20 |
| 29.9–30.1 | 2.988–2.969 | 12–17 |
| 33.6–33.8 | 2.667–2.652 | 3–4 |
| 34.4–34.6 | 2.607–2.592 | 10–14 |
| 36.9–37.0 | 2.436–2.430 | 2–3 |
| 37.6–37.9 | 2.392–2.374 | 5–8 |
| 41.45 | 2.177 | 0–2 |
| 42.2–42.4 | 2.141–2.132 | 2–3 |
| 42.8 | 2.113 | 0–1 |
| 43.4 | 2.090 | 0–1 |
| 45.0 | 2.014 | 0–1 |
| 47.5–47.8 | 1.914–1.903 | 2–4 |
| 51.3–51.6 | 1.781 | 2–3 |
| 51.95 | 1.760 | 0–1 |
| 55.5–55.8 | 1.656–1.647 | 0–2 |

EXAMPLE 46

(a) ZnAPSO-11, as prepared in example 10 was subjected to x-ray analysis. ZnAPSO-11 was determined to have a characteristic x-ray powder diffraction pattern which contains at least the d-spacings set forth below:

| 2θ | d, (Å) | 100 × I/Io |
|---|---|---|
| 6.6** | 13.44 | 10 |
| 7.7** | 11.46 | 97 |
| 8.1 | 10.89 | 26 |
| 8.45** | 10.44 | 6 |
| 9.45* | 9.35 | 60 |
| 13.3* | 6.66 | 22 |
| 13.8** | 6.43 | 4 |
| 14.9** | 5.94 | 5 |
| 15.3** | 5.80 | 8 |
| 15.7 | 5.64 | 24 |
| 16.2 | 5.47 | 3 |
| 16.65** | 5.33 | 7 |
| 18.35** | 4.83 | 16 |
| 19.0 | 4.66 | 4 |
| 19.8** | 4.49 | 4 |
| 20.45* | 4.35 | 29 |
| 21.1* | 4.20 | 100 |
| 21.55** | 4.123 | 24 |
| 22.2* | 4.008 | 32 |
| 22.75 | 3.905 | 85 |
| 23.2 | 3.830 | 45 |
| 24.2** | 3.674 | 5 |
| 24.45** | 3.643 | 3 |
| 24.8 | 3.590 | 5 |
| 26.55 | 3.355 | 14 |
| 26.8* | 3.327 | 12 |
| 27.8** | 3.212 | 4 |
| 28.7* | 3.109 | 20 |
| 29.05* | 3.075 | 5 |
| 29.8* | 3.000 | 11 |
| 30.15* | 2.966 | 11 |
| 30.75** | 2.909 | 3 |
| 31.1** | 2.874 | 5 |
| 31.6 | 2.832 | 6 |
| 32.85* | 2.725 | 11 |
| 34.3* | 2.615 | 7 |
| 34.5** | 2.598 | 5 |
| 35.9* | 2.501 | 6 |
| 36.55* | 2.459 | 5 |
| 37.85* | 2.377 | 10 |
| 39.7* | 2.270 | 1 |
| 43.0* | 2.103 | 4 |
| 44.85 | 2.022 | 3 |
| 48.85* | 1.864 | 3 |
| 50.8 | 1.797 | 1 |
| 54.8 | 1.675 | 1 |

*Peak may contain impurity
**Impurity Peak (b) The ZnAPSO-11 compositions are generally characterized by the data of Table V below.

TABLE V

| 2θ | d (Å) | Relative Intensity |
|---|---|---|
| 9.35–9.45 | 9.44–9.35 | m |
| 13.15–13.35 | 6.67–6.63 | m |
| 21.1–21.25 | 4.21–4.19 | s–vs |
| 22.75–22.85 | 3.911–3.896 | s–vs |
| 23.15–23.3 | 3.839–3.819 | w–m |
| 26.8–26.9 | 3.327–3.313 | w–m |

(c) The ZnAPSO-11 compositions for which x-ray powder diffraction data have been obtained to date have patterns which are characterized by the x-ray powder diffraction pattern shown in Table VI, below:

TABLE VI

| 2θ | d, (Å) | 100 × I/Io |
|---|---|---|
| 8.05–8.1 | 10.98–10.92 | 8–26 |
| 9.35–9.45 | 9.44–9.35 | 54–72 |
| 13.15–13.35 | 6.67–6.63 | 22–40 |
| 15.65–15.75 | 5.66–5.62 | 10–27 |
| 16.05–16.2 | 5.53–5.47 | 0–3 |
| 19.0 | 4.66 | 0–4 |
| 19.85 | 4.49–4.46 | 4–14 |
| 20.4–20.5 | 4.35–4.33 | 19–38 |
| 21.1–21.25 | 4.21–4.19 | 83–100 |
| 22.1–22.25 | 4.018–3.998 | 12–32 |
| 22.75–22.85 | 3.911–3.896 | 85–100 |
| 23.15–23.3 | 3.839–3.819 | 12–45 |
| 26.45–26.55 | 3.369–3.354 | 8–14 |
| 26.8–26.9 | 3.327–3.313 | 12–40 |
| 28.7–28.8 | 3.111–3.100 | 20–36 |
| 29.75–29.85 | 3.005–2.993 | 11–23 |
| 31.6–31.8 | 2.832–2.813 | 0–10 |
| 32.8–32.95 | 2.731–2.719 | 7–15 |
| 34.2–34.3 | 2.620–2.615 | 6–9 |
| 35.85–36.0 | 2.503–2.495 | 6–12 |
| 36.45–36.55 | 2.464–2.459 | 4–8 |
| 37.65–37.7 | 2.389–2.387 | 0–7 |
| 37.85 | 2.377 | 0–10 |
| 39.7 | 2.271 | 0–1 |
| 43.0–43.05 | 2.103–2.100 | 0–4 |
| 44.85–44.9 | 2.022–2.018 | 0–3 |
| 48.75–48.85 | 1.867–1.864 | 0–3 |
| 50.8–50.9 | 1.797–1.794 | 0–3 |
| 54.8 | 1.675 | 0–1 |

EXAMPLE 47

(a) ZnAPSO-20, as prepared in example 29, was subjected to x-ray analysis. ZnAPSO-20 was determined to have a characteristic x-ray powder diffraction pattern which contains at least the d-spacings set forth below:

| 2θ | d, (Å) | 100 × I/Io |
|---|---|---|
| 12.35* | 7.17 | 6 |
| 13.9 | 6.37 | 47 |
| 14.35* | 6.16 | 2 |
| 14.5* | 6.10 | 1 |
| 14.65* | 6.04 | 1 |
| 14.85* | 5.96 | 1 |
| 19.75 | 4.50 | 40 |
| 20.8* | 4.27 | 1 |
| 21.05* | 4.22 | 1 |
| 21.7* | 4.09 | 3 |
| 22.1 | 4.024 | 2 |
| 24.25 | 3.672 | 100 |
| 24.85* | 3.582 | 1 |
| 27.0* | 3.302 | 5 |
| 28.05 | 3.181 | 12 |
| 28.65* | 3.116 | 1 |
| 31.45 | 2.845 | 12 |
| 32.45* | 2.758 | 1 |
| 34.55 | 2.596 | 20 |
| 37.45 | 2.402 | 2 |
| 38.4* | 2.248 | 1 |
| 40.1 | 2.344 | 4 |
| 42.65 | 2.121 | 4 |
| 45.13* | 2.009 | 1 |
| 47.4 | 1.917 | 5 |
| 49.35* | 1.846 | 1 |
| 51.8 | 1.765 | 9 |

*Impurity peak (b) The ZnAPSO-20 compositions are generally characterized by the data of Table VII below:

TABLE VII

| 2θ | d, (Å) | Relative Intensity |
|---|---|---|
| 13.85–14.0 | 6.39–6.33 | m |
| 19.65–19.8 | 4.52–4.48 | m |
| 24.15–24.3 | 3.685–3.663 | vs |
| 28.0–28.15 | 3.187–3.170 | w |
| 31.25–31.5 | 2.853–2.840 | w |
| 34.5–34.65 | 2.600–2.589 | w–m |

(c) The ZnAPSO-20 compositions for which x-ray powder diffraction data have been obtained to date have patterns which are characterized by the x-ray powder diffraction pattern shown in Table VIII, below:

TABLE VIII

| 2θ | d, (Å) | 100 × I/Io |
|---|---|---|
| 13.85–14.0 | 6.39–6.33 | 45–47 |
| 19.65–19.8 | 4.52–4.48 | 40–41 |
| 22.0–22.15 | 4.040–4.013 | 2–3 |
| 24.15–24.3 | 3.685–3.663 | 100 |
| 28.0–28.15 | 3.187–3.170 | 12–13 |
| 31.35–31.5 | 2.853–2.840 | 11–12 |
| 34.5–34.65 | 2.600–2.589 | 16–20 |
| 37.35–37.5 | 2.408–2.398 | 2 |
| 40.0–40.2 | 2.254–2.243 | 4 |
| 42.55–42.7 | 2.125–2.118 | 4 |
| 47.35–47.5 | 1.920–1.914 | 5 |
| 51.75–51.9 | 1.767–1.762 | 8–9 |

EXAMPLE 48

(a) ZnAPSO-31, as prepared in example 14, was subjected to x-ray analysis. ZnAPSO-31 was determined to have a characteristic x-ray powder diffraction pattern which contains at least the d-spacings set forth below:

| 2θ | d, (Å) | 100 × I/Io |
|---|---|---|
| 6.6** | 13.40 | 14 |
| 7.7** | 11.45 | 10 |
| 8.1** | 10.94 | 11 |
| 8.5 | 10.40 | 50 |
| 9.5* | 9.32 | 8 |
| 9.85* | 8.96 | 2 |
| 12.45** | 7.12 | 25 |
| 13.4 | 6.60 | 10 |
| 17.05 | 5.21 | 5 |
| 17.4** | 5.10 | 3 |
| 18.25 | 4.86 | 8 |
| 20.3 | 4.38 | 52 |
| 21.3* | 4.17 | 16 |
| 21.6** | 4.11 | 10 |
| 22.0 | 4.036 | 30 |
| 22.6 | 3.394 | 100 |
| 23.55* | 3.779 | 2 |
| 24.25** | 3.668 | 3 |
| 25.15* | 3.543 | 4 |
| 27.0** | 3.302 | 3 |
| 27.75* | 3.213 | 12 |
| 27.95 | 3.192 | 13 |
| 28.2* | 3.162 | 4 |
| 28.7** | 3.109 | 3 |
| 29.75 | 3.004 | 10 |
| 30.3 | 2.950 | 4 |
| 31.75 | 2.810 | 20 |
| 32.95 | 2.718 | 4 |
| 34.2** | 2.623 | 3 |
| 35.15 | 2.554 | 12 |
| 35.7* | 2.515 | 3 |
| 35.9* | 2.500 | 3 |
| 36.2 | 2.481 | 4 |
| 37.25* | 2.413 | 3 |
| 37.65* | 2.390 | 2 |
| 38.25 | 2.353 | 3 |
| 39.3 | 2.291 | 2 |
| 40.3 | 2.238 | 2 |
| 45.0* | 2.014 | 2 |
| 46.6 | 1.949 | 4 |
| 47.4** | 1.918 | 2 |
| 48.6 | 1.873 | 2 |
| 51.5 | 1.774 | 7 |

*peak may contain impurity
**impurity peak (b) The ZnAPSO-31 compositions are generally characterized by the data of Table IX below:

TABLE IX

| 2θ | d, (Å) | Relative Intensity |
|---|---|---|
| 8.4–8.5 | 10.35–10.40 | m |
| 20.2–20.3 | 4.40–4.37 | m |
| 21.3 | 4.171 | w |
| 22.0 | 4.036 | m |
| 22.5–22.6 | 3.952–3.934 | vs |
| 31.6–31.75 | 2.831–2.820 | w–m |

(c) The ZnAPSO-31 compositions for which x-ray powder diffraction data have been obtained to date have patterns which are characterized by the x-ray powder diffraction pattern shown in Table X, below:

TABLE X

| 2θ | d, (Å) | 100 × I/Io |
|---|---|---|
| 8.4–8.5 | 10.53–10.40 | 50–53 |
| 9.45–9.5 | 9.35–9.32 | 7–8 |
| 13.2–13.4 | 6.76–6.60 | 10–11 |
| 18.2–18.25 | 4.87–4.86 | 5–8 |
| 20.2–20.3 | 4.39–4.37 | 49–52 |
| 21.3 | 4.171 | 16–18 |
| 22.0 | 4.036 | 30 |
| 22.5–22.6 | 3.952–3.934 | 100 |
| 26.9–27.0 | 3.314–3.302 | 3–7 |
| 27.95–28.25 | 3.192–3.529 | 13–17 |
| 29.6–29.7 | 3.018–3.008 | 8–10 |

TABLE X-continued

| 2θ | d, (Å) | 100 × I/Io |
|---|---|---|
| 30.2–30.3 | 2.959–2.950 | 0–4 |
| 31.6–31.75 | 2.831–2.820 | 18–20 |
| 32.95 | 2.718 | 4–9 |
| 35.15–35.2 | 2.554–2.550 | 12 |
| 36.1–36.2 | 2.489–2.481 | 4–7 |
| 37.25–37.35 | 2.413–2.409 | 2–3 |
| 38.25 | 2.353 | 3 |
| 39.3 | 2.291 | 2 |
| 40.3 | 2.238 | 2 |
| 46.6–46.65 | 1.949–1.948 | 4–6 |
| 47.4–47.45 | 1.918–1.916 | 2–4 |
| 51.5 | 1.774 | 7 |

EXAMPLE 49

(a) ZnAPSO-34, as prepared in example 24, was subjected to x-ray analysis. ZnAPSO-34 was determined to have a characteristic x-ray powder diffraction pattern which contains at least the d-spacings set forth below:

TABLE XIII

| 2θ | d, (Å) | 100 × I/Io |
|---|---|---|
| 9.6 | 9.19 | 100 |
| 12.95 | 6.84 | 16 |
| 14.2 | 6.25 | 14 |
| 16.1 | 5.50 | 42 |
| 18.1 | 4.90 | 22 |
| 20.65 | 4.30 | 91 |
| 22.4 | 3.978 | 5 |
| 23.15 | 3.842 | 5 |
| 25.3 | 3.521 | 25 |
| 25.9 | 3.437 | 18 |
| 27.7 | 3.218 | 5 |
| 28.45 | 3.135 | 6 |
| 29.65 | 3.015 | 5 |
| 30.6 | 2.920 | 33 |
| 31.3 | 2.856 | 23 |
| 32.5 | 2.755 | 2 |
| 34.45 | 2.602 | 7 |
| 36.4 | 2.468 | 5 |
| 38.8 | 2.320 | 4 |
| 39.75 | 2.267 | 5 |
| 43.15 | 2.097 | 4 |
| 43.55* | 2.077 | 4 |
| 47.65 | 1.908 | 5 |
| 49.10 | 1.856 | 8 |
| 49.9 | 1.827 | 4 |
| 51.0 | 1.791 | 4 |
| 53.15 | 1.723 | 3 |
| 54.65 | 1.679 | 3 |
| 55.9 | 1.645 | 3 |

*impurity peak (b) A portion of the as-synthesized ZnAPSO-34 of part (a) was calcined in air at 500° C. for about 2 hours. The calcined product was characterized by the x-ray powder diffraction pattern below:

| 2θ | d, (Å) | 100 × I/Io |
|---|---|---|
| 9.55 | 9.27 | 100 |
| 12.95 | 6.85 | 24 |
| 16.15 | 5.49 | 13 |
| 17.95 | 4.94 | 10 |
| 20.75 | 4.28 | 30 |
| 22.2 | 4.004 | 2 |
| 23.25 | 3.828 | 5 |
| 25.2 | 3.533 | 9 |
| 26.15 | 3.411 | 12 |
| 28.45 | 3.138 | 4 |
| 30.9 | 2.896 | 16 |
| 31.35 | 2.852 | 9 |

(c) The ZnAPSO-34 compositions are generally characterized by the data of Table XI below.

TABLE XI

| 2θ | d, (Å) | Relative Intensity |
|---|---|---|
| 9.4–9.8 | 9.41–9.03 | m–vs |
| 12.7–13.2 | 6.97–6.71 | w–m |
| 15.8–16.2 | 5.61–5.47 | w–m |
| 20.5–20.9 | 4.33–4.25 | m–vs |
| 25.0–25.3 | 3.562–3.520 | vw–m |
| 30.5–30.9 | 2.931–2.894 | w–m |

(d) The ZnAPSO-34 compositions for which x-ray powder diffraction data have been obtained to date have patterns which are characterized by the x-ray powder diffraction pattern shown in Table XII, below:

TABLE XII

| 2θ | d, (Å) | 100 × I/Io |
|---|---|---|
| 9.4–9.8 | 9.41–9.03 | 77–100 |
| 12.7–13.2 | 6.97–6.71 | 16–31 |
| 14.0–14.3 | 6.33–6.19 | 0–22 |
| 15.8–16.2 | 5.61–5.47 | 16–47 |
| 17.8–18.2 | 4.98–4.87 | 13–29 |
| 20.5–20.9 | 4.33–4.25 | 36–100 |
| 22.2–22.5 | 4.004–3.952 | 5.8 |
| 23.0–23.3 | 3.867–3.818 | 5–6 |
| 25.0–25.3 | 3.562–3.520 | 9–32 |
| 25.7–26.25 | 3.466–3.395 | 12–20 |
| 27.45–27.7 | 3.249–3.220 | 5–8 |
| 28.1–28.45 | 3.175–3.137 | 4–8 |
| 29.4–29.8 | 3.038–2.998 | 0–5 |
| 30.5–30.9 | 2.931–2.894 | 16–35 |
| 31.0–31.65 | 2.885–2.827 | 9–25 |
| 32.2–32.5 | 2.780–2.755 | 0–2 |
| 34.3–34.8 | 2.614–2.578 | 5–8 |
| 36.1–36.4 | 2.488–2.468 | 0–5 |
| 38.65–38.8 | 2.330–2.321 | 0–4 |
| 39.5–39.8 | 2.281–2.265 | 4–7 |
| 43.0–43.4 | 2.103–2.085 | 4 |
| 47.5–48.0 | 1.914–1.895 | 3–6 |
| 48.8–49.1 | 1.866–1.855 | 8–10 |
| 49.9 | 1.859 | 0–4 |
| 50.8–51.0 | 1.797–1.791 | 0–4 |
| 53.1–53.15 | 1.725–1.723 | 0–3 |
| 54.5–54.8 | 1.684–1.675 | 0–3 |
| 55.8–55.9 | 1.647–1.645 | 0–4 |

EXAMPLE 50

(a) ZnAPSO-35, as prepared in example 33, was subjected to x-ray analysis. ZnAPSO-35 was determined to have a characteristic x-ray powder diffraction pattern which contains at least the d-spacings set forth below:

| 2θ | d, (Å) | 100 × I/Io |
|---|---|---|
| 8.6 | 10.27 | 20 |
| 10.5* | 8.44 | sh |
| 10.95 | 8.08 | 47 |
| 11.35 | 7.80 | 4 |
| 13.30 | 6.66 | 39 |
| 15.9 | 5.57 | 10 |
| 17.3 | 5.13 | 72 |
| 17.8 | 4.98 | sh |
| 21.15 | 4.20 | 48 |
| 21.9 | 4.06 | 100 |
| 23.15 | 3.841 | 19 |
| 23.65 | 3.762 | 3 |
| 25.05 | 3.552 | 4 |
| 26.8 | 3.325 | 22 |
| 28.7 | 3.107 | 30 |
| 29.1 | 3.069 | sh |
| 32.1 | 2.788 | 43 |
| 34.75 | 2.582 | 9 |
| 35.5 | 2.530 | 3 |

-continued

| 2θ | d, (Å) | 100 × I/Io |
|---|---|---|
| 35.8 | 2.507 | 5 |
| 37.75 | 2.382 | 5 |
| 39.35 | 2.889 | 4 |
| 42.35 | 2.134 | 6 |
| 43.15 | 2.096 | 4 |
| 48.6 | 1.873 | 11 |
| 49.4 | 1.845 | 8 |
| 51.55 | 1.773 | 6 |
| 55.3 | 1.661 | 6 |

*impurity peak (b) A portion of the as-synthesized ZnAPSO-35 of part (a) was calcined in air at 500° C. for about 1.75 hours. The calcined product was characterized by the x-ray powder diffraction pattern below:

| 2θ | d, (Å) | 100 × I/Io |
|---|---|---|
| 7.45* | 11.85 | 10 |
| 8.7 | 10.15 | 22 |
| 11.0 | 8.04 | 91 |
| 13.5 | 6.55 | 100 |
| 17.45 | 5.08 | 35 |
| 21.0 | 4.23 | 21 |
| 22.15 | 4.011 | 60 |
| 23.5 | 3.782 | 19 |
| 25.15 | 3.542 | 13 |
| 27.2 | 3.278 | 20 |
| 28.6 | 3.122 | 28 |
| 29.35 | 3.041 | 14 |
| 32.45 | 2.759 | 28 |

*impurity peak (c) The ZnAPSO-35 compositions obtained to date have patterns which are generally characterized by the data of Table XIII below.

TABLE XIII

| 2θ | d, (Å) | Relative Intensity |
|---|---|---|
| 10.8–11.0 | 8.19–8.04 | m–vs |
| 13.30–13.5 | 6.66–6.56 | m–vs |
| 17.2–17.45 | 5.16–5.08 | m |
| 20.95–21.2 | 4.24–4.19 | m |
| 21.9–22.15 | 4.06–4.01 | m–vs |
| 32.0–32.5 | 2.797–2.755 | m |

(d) The ZnAPSO-35 composition for which x-ray powder diffraction data have been obtained to date have patterns which are characterized by the x-ray powder diffraction pattern shown in Table XIV below:

| 2θ | d, (Å) | 100 × I/Io |
|---|---|---|
| 8.6–8.7 | 10.27–10.16 | 18–22 |
| 10.8–11.0 | 8.19–8.04 | 43–91 |
| 11.35 | 7.80 | 0–4 |
| 13.30–13.5 | 6.66–6.56 | 39–100 |
| 15.8–15.9 | 5.61–5.57 | 0–10 |
| 17.2–17.45 | 5.16–5.08 | 35–75 |
| 17.8–17.9 | 4.98–4.96 | 0–sh |
| 20.95–21.2 | 4.24–4.19 | 21–49 |
| 21.9–22.15 | 4.06–4.01 | 60–100 |
| 23.0–23.5 | 3.867–3.786 | 0–19 |
| 23.65 | 3.762 | 0–3 |
| 24.85–25.15 | 3.583–3.541 | 4–13 |
| 26.6–27.2 | 3.351–3.278 | 20–22 |
| 28.5–28.8 | 3.132–3.100 | 26–30 |
| 29.1–29.35 | 3.069–3.043 | sh–14 |
| 32.0–32.5 | 2.797–2.755 | 28–43 |
| 34.55–34.9 | 2.596–2.571 | 0–9 |
| 35.7–35.8 | 2.515–2.507 | 0–5 |
| 37.75 | 2.382 | 0–5 |
| 39.35 | 2.889 | 0–4 |
| 42.1–42.35 | 2.146–2.134 | 0–6 |
| 43.0–43.2 | 2.103–2.094 | 0–4 |
| 48.5–48.7 | 1.877–1.870 | 0–11 |
| 49.35–49.4 | 1.847–1.845 | 0–8 |
| 51.4–51.6 | 1.778–1.771 | 0–7 |
| 55.3–55.4 | 1.661–1.658 | 0–6 |

EXAMPLE 51

(a) ZnAPSO-36, as prepared in example 1, was subjected to x-ray analysis. ZnAPSO-36 was determined to have a characteristic x-ray powder diffraction pattern which contains at least the d-spacings set forth below:

| 2θ | d, (Å) | 100 × I/Io |
|---|---|---|
| 7.45** | 11.85 | 76 |
| 7.95 | 11.13 | 100 |
| 8.2 | 10.76 | sh |
| 12.9** | 6.87 | 3 |
| 13.6 | 6.52 | 4 |
| 14.9** | 5.95 | 10 |
| 15.9 | 5.58 | 10 |
| 16.45 | 5.38 | 25 |
| 19.1 | 4.64 | 16 |
| 19.75** | 4.50 | 15 |
| 20.8* | 4.27 | 32 |
| 21.05** | 4.22 | sh |
| 21.75 | 4.09 | 14 |
| 22.1 | 4.025 | 14 |
| 22.4* | 3.966 | 24 |
| 23.0 | 3.863 | 3 |
| 23.95 | 3.716 | 5 |
| 25.9** | 3.440 | 9 |
| 27.3 | 3.269 | 11 |
| 28.35 | 3.147 | 7 |
| 29.05* | 3.074 | 9 |
| 30.0** | 2.978 | 8 |
| 30.35 | 2.944 | 4 |
| 32.0 | 2.796 | 8 |
| 33.2 | 2.698 | 1 |
| 33.65** | 2.663 | 1 |
| 34.5** | 2.599 | 6 |
| 34.8 | 2.575 | 7 |
| 35.9 | 2.500 | 2 |
| 37.75 | 2.383 | 2 |
| 40.3 | 2.237 | 2 |
| 41.45 | 2.178 | 2 |
| 42.2 | 2.142 | 1 |
| 47.6* | 1.910 | 2 |
| 51.35 | 1.779 | 2 |
| 54.0 | 1.697 | 1 |
| 55.65 | 1.652 | 2 |

*peak may contain impurity
**impurity peak (b) The ZnAPSO-36 compositions obtained to date have patterns which are generally characterized by the data of Table XV below.

TABLE XV

| 2θ | d, (Å) | Relative Intensity |
|---|---|---|
| 7.45–8.0 | 11.14–11.04 | vs |
| 16.45–16.5 | 5.38–5.36 | w–m |
| 19.1–19.2 | 4.65–4.62 | w–m |
| 20.8–20.9 | 4.28–4.25 | w–m |
| 21.75–21.8 | 4.09–4.08 | w |
| 22.05–22.15 | 4.027–4.017 | w |

(c) The ZnAPSO-36 compositions for which x-ray powder diffraction data have been obtained to date have patterns which are characterized by the x-ray powder diffraction pattern shown in Table XVI below:

TABLE XVI

| 2θ | d, (Å) | 100 × I/Io |
|---|---|---|
| 7.45–8.0 | 11.14–11.04 | 100 |
| 8.2–8.3 | 10.76–10.68 | 0–sh |
| 13.55–13.6 | 6.53–6.50 | 3–4 |
| 15.85–15.95 | 5.60–5.56 | 10–12 |
| 16.45–16.5 | 5.38–5.36 | 18–31 |
| 19.1–19.2 | 4.65–4.62 | 19–22 |
| 20.8–20.9 | 4.28–4.25 | 17–39 |
| 21.75–21.8 | 4.09–4.08 | 10–17 |
| 22.05–22.15 | 4.027–4.017 | 14–17 |
| 23.0–23.05 | 3.865–3.859 | 3–4 |
| 23.85–24.0 | 3.728–3.707 | 3–6 |
| 27.25–27.35 | 3.273–3.260 | 9–15 |
| 28.3–28.4 | 3.152–3.142 | 6–9 |
| 30.1–30.4 | 2.970–2.940 | 4–6 |
| 31.95–32.1 | 2.803–2.788 | 6–11 |
| 33.2–33.6 | 2.698–2.665 | 1–2 |
| 34.75–34.9 | 2.580–2.572 | 7–10 |
| 35.85–35.95 | 2.504–2.497 | 2–6 |
| 37.75–37.8 | 2.384–2.380 | 2 |
| 40.15–40.4 | 2.246–2.232 | 1–3 |
| 41.45–41.5 | 2.180–2.176 | 1–2 |
| 42.2–42.3 | 2.142–2.137 | 0–2 |
| 51.4–51.45 | 1.779–1.776 | 2 |
| 54.0 | 1.697 | 0–1 |
| 55.4–55.8 | 1.658–1.648 | 1–2 |

EXAMPLE 52

(a) ZnAPSO-39, as referred to in example 9, was subjected to x-ray analysis. ZnAPSO-39 was determined to have a characteristic x-ray powder diffraction pattern which contains at least the d-spacings set forth below:

| 2θ | d, (Å) | 100 × I/Io |
|---|---|---|
| 6.5** | 13.59 | 17 |
| 7.65** | 11.56 | 173 |
| 8.05** | 10.99 | 12 |
| 8.35** | 10.58 | 4 |
| 9.35* | 9.44 | 72 |
| 13.25* | 6.67 | 35 |
| 13.7** | 6.46 | 8 |
| 14.9** | 5.95 | 8 |
| 15.2** | 5.82 | 12 |
| 15.65** | 5.66 | 12 |
| 16.6** | 5.34 | 13 |
| 18.3 | 4.85 | 36 |
| 19.8** | 4.48 | 4 |
| 20.4** | 4.35 | 19 |
| 21.1* | 4.21 | 83 |
| 21.5** | 4.13 | 36 |
| 22.1** | 4.018 | 12 |
| 22.75* | 3.911 | 100 |
| 23.15** | 3.839 | 19 |
| 23.95** | 3.716 | 4 |
| 24.2** | 3.681 | 9 |
| 24.8** | 3.593 | 3 |
| 26.45** | 3.369 | 8 |
| 26.8* | 3.324 | 21 |
| 27.75** | 3.215 | 6 |
| 28.2** | 3.162 | 5 |
| 28.7* | 3.111 | 19 |
| 29.7* | 3.005 | 15 |
| 30.1* | 2.970 | 22 |
| 30.6** | 2.922 | 4 |
| 31.05** | 2.881 | 7 |
| 32.8* | 2.731 | 8 |
| 34.3* | 2.615 | 6 |
| 34.55** | 2.597 | 10 |
| 35.9** | 2.502 | 8 |
| 36.45* | 2.464 | 4 |
| 38.05* | 2.365 | 5 |

-continued

| 2θ | d, (Å) | 100 × I/Io |
|---|---|---|
| 40.7* | 2.217 | 4 |

*peak may contain impurity
**impurity peak (b) The ZnAPSO-39 compositions are generally characterized by the data of Table XVII below.

TABLE XVII

| 2θ | d, (Å) | Relative Intensity |
|---|---|---|
| 9.35–9.45 | 9.46–9.36 | m |
| 13.15–13.35 | 6.73–6.63 | m |
| 18.3–18.4 | 4.85–4.82 | w–m |
| 21.1–21.2 | 4.21–4.19 | s–vs |
| 22.75–22.85 | 3.909–3.892 | s–vs |
| 26.8–26.9 | 3.389–3.314 | w–m |

(c) The ZnAPSO-39 compositions for which x-ray powder diffraction data have been obtained to date have patterns which are characterized by the x-ray powder diffraction pattern shown in Table XVIII below:

| 2θ | d, (Å) | 100 × I/Io |
|---|---|---|
| 9.35–9.45 | 9.46–9.36 | 60–72 |
| 13.15–13.35 | 6.73–6.63 | 22–40 |
| 18.3–18.4 | 4.85–4.82 | 16–40 |
| 21.1–21.2 | 4.21–4.19 | 83–100 |
| 22.75–22.85 | 3.909–3.892 | 85–100 |
| 26.8–26.9 | 3.389–3.314 | 12–40 |
| 28.2–28.3 | 3.164–3.153 | 5–8 |
| 28.7–28.8 | 3.110–3.100 | 19–20 |
| 29.7–29.8 | 3.008–2.998 | 11–32 |
| 30.1–30.2 | 2.979–2.959 | 11–25 |
| 32.8–32.95 | 2.730–2.718 | 8–12 |
| 34.5–34.65 | 2.600–2.589 | 5–6 |
| 36.45–36.5 | 2.465–2.462 | 4–12 |
| 37.85–38.1 | 2.377–2.362 | 3–10 |
| 40.6–40.95 | 2.222–2.204 | 0–4 |

EXAMPLE 53

(a) ZnAPSO-43, as referred to in example 28, was subjected to x-ray analysis. ZnAPSO-43 was determined to have a characteristic x-ray powder diffraction pattern which contains at least the d-spacings set forth below:

| 2θ | d, (Å) | 100 × I/Io |
|---|---|---|
| 12.45 | 7.11 | 76 |
| 14.0* | 6.32 | 194 |
| 16.95 | 5.24 | 8 |
| 19.8* | 4.48 | 160 |
| 20.95 | 4.24 | 13 |
| 21.15* | 4.20 | 13 |
| 21.85 | 4.07 | 48 |
| 22.15* | 4.010 | 8 |
| 24.3* | 3.659 | 400 |
| 27.1 | 3.291 | 100 |
| 28.15* | 3.171 | 52 |
| 28.75 | 3.104 | 4 |
| 31.55* | 2.837 | 49 |
| 32.55 | 2.751 | 20 |
| 32.75* | 2.733 | 9 |
| 34.25* | 2.620 | 8 |
| 34.65* | 2.590 | 68 |
| 37.5* | 2.399 | 8 |
| 38.5* | 2.340 | 6 |
| 40.2* | 2.244 | 16 |
| 41.2 | 2.190 | 4 |
| 42.7* | 2.117 | 16 |
| 45.1 | 2.010 | 8 |

-continued

| 2θ | d, (Å) | 100 × I/Io |
|---|---|---|
| 47.5* | 1.914 | 18 |
| 49.45* | 1.843 | 7 |
| 51.15 | 1.787 | 7 |
| 51.9* | 1.761 | 36 |
| 53.8 | 1.704 | 7 |

*Impurity peak (b) ZnAPSO-43 compositions are generally characterized by the data of Table XIX below:

TABLE XIX

| 2θ | d, (Å) | Relative Intensity |
|---|---|---|
| 12.3–12.45 | 7.20–7.11 | m–vs |
| 16.8–16.95 | 5.28–5.23 | vw–w |
| 21.7–21.85 | 4.095–4.068 | vw–m |
| 26.95–27.1 | 3.308–3.291 | s–vs |
| 32.4–32.55 | 2.763–2.751 | w–m |

(c) The ZnAPSO-43 compositions for which x-ray powder diffraction data have been obtained to date have patterns which are characterized by the x-ray powder diffraction pattern shown in Table XX below:

TABLE XX

| 2θ | d, (Å) | 100 × I/Io |
|---|---|---|
| 12.3–12.45 | 7.20–7.11 | 66–100 |
| 16.8–16.95 | 5.28–5.23 | 0–10 |
| 20.8–20.95 | 4.27–4.24 | 10–13 |
| 21.7–21.85 | 4.095–4.068 | 0–48 |
| 26.95–27.1 | 3.308–3.290 | 82–100 |
| 28.65–28.75 | 3.116–3.105 | 11–23 |
| 32.4–32.55 | 2.763–2.751 | 18–20 |
| 41.2 | 2.191 | 0–4 |
| 44.95–45.1 | 2.017–2.010 | 8–15 |
| 50.95–51.15 | 1.792–1.786 | 0–7 |
| 53.7–53.8 | 1.710–1.707 | 0–8 |

EXAMPLE 54

(a) ZnAPSO-44 as prepared in example 34, was subjected to x-ray analysis. ZnAPSO-44 was determined to have a characteristic x-ray powder diffraction pattern which contains at least the d-spacings set forth below:

| 2θ | d, (Å) | 100 × I/Io |
|---|---|---|
| 4.95* | 17.93 | 11 |
| 8.75* | 10.09 | sh |
| 9.25* | 9.56 | sh |
| 9.55 | 9.25 | 100 |
| 13.05 | 6.77 | 13 |
| 13.8 | 6.41 | 3 |
| 16.15 | 5.49 | 21 |
| 17.4 | 5.10 | 3 |
| 19.05 | 4.65 | 7 |
| 19.6* | 4.53 | 2 |
| 20.8 | 4.27 | 46 |
| 21.8 | 4.08 | 18 |
| 22.65 | 3.923 | 4 |
| 23.15 | 3.845 | 5 |
| 24.45 | 3.638 | 47 |
| 26.25 | 3.395 | 14 |
| 27.3* | 3.266 | 1 |
| 27.9 | 3.197 | 7 |
| 29.8 | 2.999 | 3 |
| 30.15 | 2.962 | 13 |
| 30.9 | 2.895 | 31 |
| 32.65 | 2.745 | 2 |
| 33.0 | 2.716 | 6 |
| 34.9 | 2.571 | 2 |
| 35.15 | 2.553 | 2 |
| 35.6 | 2.523 | 9 |
| 38.7 | 2.329 | 2 |

-continued

| 2θ | d, (Å) | 100 × I/Io |
|---|---|---|
| 39.25 | 2.295 | 2 |
| 40.1 | 2.247 | 1 |
| 42.25 | 2.139 | 3 |
| 42.55 | 2.124 | 2 |
| 43.7 | 2.072 | 1 |
| 48.2 | 1.887 | 3 |
| 48.8 | 1.866 | 4 |
| 50.4 | 1.811 | 5 |
| 52.0 | 1.759 | 1 |
| 54.0 | 1.698 | 7 |

*Impurity Peak (b) A portion of the as-synthesized ZnAPSO-44 part (a) was calcined in air at 500° C. for about 67 hours. The calcined product was characterized by the x-ray powder diffraction pattern below:

| 2θ | d, (Å) | 100 × I/Io |
|---|---|---|
| 9.6 | 9.23 | 100 |
| 13.0 | 6.81 | 34 |
| 14.05 | 6.29 | 5 |
| 16.2 | 5.48 | 16 |
| 17.95 | 4.95 | 30 |
| 20.3** | 4.37 | 22 |
| 20.8 | 4.27 | 52 |
| 21.4 | 4.15 | 32 |
| 22.3 | 3.987 | 7 |
| 22.75* | 3.906 | 7 |
| 23.25 | 3.826 | 10 |
| 24.75** | 3.599 | 5 |
| 25.15 | 3.538 | 22 |
| 26.15 | 3.406 | 11 |
| 28.4 | 3.142 | 9 |
| 28.75** | 3.107 | 7 |
| 30.95 | 2.888 | 23 |
| 31.35* | 2.852 | 15 |
| 35.3* | 2.542 | 9 |

*Peak may contain impurity
**Impurity peak (c) The ZnAPSO-44 compositions are generally characterized by the data of Table XXI below:

TABLE XXI

| 2θ | d, (Å) | Relative Intensity |
|---|---|---|
| 9.4–9.55 | 9.41–9.26 | vs |
| 12.9–13.05 | 6.86–6.78 | vw–m |
| 20.65–20.8 | 4.30–4.27 | m |
| 21.4–21.8 | 4.15–4.08 | w–m |
| 24.3–25.15 | 3.663–3.541 | m |
| 30.75–30.95 | 2.908–2.889 | m |

(d) The ZnAPSO-44 compositions for which x-ray powder diffraction data have been obtained to date have patterns which are characterized by the x-ray powder diffraction pattern shown in Table XXII below:

| 2θ | d, (Å) | 100 × I/Io |
|---|---|---|
| 9.4–9.55 | 9.41–9.25 | 100 |
| 12.9–13.05 | 6.86–6.78 | 8–34 |
| 13.6–14.05 | 6.51–6.30 | 3–5 |
| 16.0–16.2 | 5.54–5.47 | 14–21 |
| 17.25–17.95 | 5.14–4.94 | 0–6 |
| 18.95–19.05 | 4.68–4.66 | 0–5 |
| 20.65–20.8 | 4.30–4.27 | 35–52 |
| 21.4–21.8 | 4.15–4.08 | 18–32 |
| 22.55–22.65 | 3.943–3.926 | 4 |
| 23.15–23.25 | 3.842–3.826 | 5–10 |
| 24.3–25.15 | 3.663–3.541 | 22–47 |
| 26.1–26.25 | 3.414–3.395 | 8–14 |
| 27.7–28.4 | 3.220–3.143 | 7–9 |

-continued

| 2θ | d, (Å) | 100 × I/Io |
|---|---|---|
| 29.8 | 2.998– | 0–3 |
| 30.05–30.15 | 2.974 | 0–13 |
| 30.75–30.95 | 2.908–2.889 | 23–31 |
| 32.65–32.8 | 2.743–2.730 | 0–3 |
| 33.0 | 2.714 | 0–6 |
| 34.9 | 2.571 | 0–2 |
| 35.15 | 2.553 | 0–2 |
| 35.3–35.6 | 2.543–2.522 | 9–10 |
| 38.7 | 2.327–2.327 | 0–2 |
| 39.3–40.2 | 2.292–2.243 | 0–2 |
| 40.1 | 2.249 | 0–1 |
| 42.1–42.3 | 2.146–2.137 | 0–3 |
| 42.55 | 2.127 | 0–2 |
| 43.7 | 2.071 | 0–1 |
| 48.2 | 1.888 | 0–3 |
| 48.65–48.8 | 1.872–1.866 | 0–5 |
| 50.2–50.4 | 1.817–1.811 | 0–5 |
| 52.0 | 1.759 | 0–1 |
| 53.8–54.0 | 1.704–1.698 | 0–7 |

EXAMPLE 55

(a) ZnAPSO-46, as referred to in example 8 was subjected to x-ray analysis. ZnAPSO-46 was determined to have a characteristic x-ray powder diffraction pattern which contains at least the d-spacings set forth below:

| 2θ | d, (Å) | 100 × I/Io |
|---|---|---|
| 6.6 | 13.39 | 8 |
| 7.75 | 11.42 | 100 |
| 8.1** | 10.90 | 3 |
| 9.45** | 9.34 | 18 |
| 10.2 | 8.67 | 1 |
| 13.35* | 6.63 | 10 |
| 13.8 | 6.41 | 4 |
| 14.95 | 5.92 | 4 |
| 15.75** | 5.62 | 3 |
| 16.7 | 5.31 | 7 |
| 17.5 | 5.07 | 1 |
| 18.4** | 4.83 | 10 |
| 19.85 | 4.47 | 3 |
| 20.5* | 4.33 | 6 |
| 21.25** | 4.19 | 25 |
| 21.6 | 4.12 | 18 |
| 22.25** | 3.998 | 3 |
| 22.8 | 3.896 | 32 |
| 23.3** | 3.818 | 4 |
| 24.05 | 3.700 | 3 |
| 24.25* | 3.669 | 5 |
| 25.3* | 3.523 | 1 |
| 26.55** | 3.354 | 3 |
| 26.9 | 3.313 | 10 |
| 27.8 | 3.207 | 3 |
| 28.3 | 3.152 | 2 |
| 28.8* | 3.100 | 8 |
| 29.85* | 2.993 | 6 |
| 30.2** | 2.961 | 7 |
| 31.15 | 2.870 | 3 |
| 31.8* | 2.813 | 1 |
| 32.95* | 2.719 | 3 |
| 34.3* | 2.612 | 2 |
| 34.65** | 2.590 | 3 |
| 36.0* | 2.495 | 3 |
| 36.55 | 2.459 | 2 |
| 36.8* | 2.442 | 1 |
| 37.3 | 2.410 | 1 |
| 38.1** | 2.361 | 1 |
| 39.7* | 2.271 | 1 |
| 40.95* | 2.204 | 1 |
| 43.2** | 2.093 | 1 |
| 44.1* | 2.054 | 1 |
| 46.1* | 1.969 | 1 |
| 47.65* | 1.908 | 1 |
| 49.45** | 1.844 | 1 |
| 49.65* | 1.836 | 1 |
| 51.55* | 1.772 | 1 |

-continued

| 2θ | d, (Å) | 100 × I/Io |
|---|---|---|
| 52.45* | 1.745 | 1 |

*Peak may contain impurity
**Impurity peak (b) The ZnAPSO-46 compositions are characterized by the data of Table XXIII below:

TABLE XXIII

| 2θ | d, (Å) | Relative Intensity |
|---|---|---|
| 7.6–7.75 | 11.63–11.42 | vs |
| 13.1–13.35 | 6.76–6.63 | w–m |
| 21.5–21.6 | 4.13–4.12 | w–m |
| 22.6–22.85 | 3.934–3.896 | m |
| 26.75–27.0 | 3.333–3.302 | w |

(c) The ZnAPSO-46 compositions for which x-ray powder diffraction data have been obtained to date have patterns which are characterized by the x-ray powder diffraction pattern shown in Table XXIV below:

TABLE XXIV

| 2θ | d, (Å) | 100 × I/Io |
|---|---|---|
| 6.5–6.7 | 13.60–13.19 | 7–10 |
| 7.6–7.75 | 11.63–11.42 | 100 |
| 10.2 | 8.67 | 0–1 |
| 13.1–13.35 | 6.76–6.63 | 10–20 |
| 13.7–13.8 | 6.46–6.41 | 4–5 |
| 14.9–15.0 | 5.95–5.91 | 4–5 |
| 15.2–15.35 | 5.83–5.77 | 5–7 |
| 16.6–16.8 | 5.34–5.28 | 7 |
| 17.35–17.5 | 5.11–5.07 | 0–1 |
| 19.7–20.0 | 4.51–4.44 | 2–3 |
| 20.3–20.5 | 4.37–4.33 | 6–11 |
| 21.5–21.6 | 4.13–4.12 | 18–21 |
| 22.6–22.85 | 3.934–3.896 | 32–58 |
| 23.9–24.05 | 3.723–3.700 | 2–3 |
| 25.1–25.3 | 3.548–3.520 | 0–1 |
| 26.75–27.0 | 3.333–3.302 | 10–12 |
| 27.7–28.0 | 3.220–3.187 | 3–4 |
| 28.2–28.3 | 3.175–3.152 | 2–3 |
| 28.6–28.9 | 3.121–3.089 | 8–11 |
| 29.7–29.9 | 3.008–2.988 | 6–9 |
| 31.0–31.15 | 2.885–2.870 | 3–4 |
| 31.6–31.8 | 2.831–2.813 | 0–1 |
| 32.8–33.2 | 2.730–2.706 | 3–4 |
| 34.15–34.4 | 2.626–2.607 | 2–4 |
| 35.8–36.0 | 2.508–2.495 | 3–4 |
| 36.45–36.55 | 2.464–2.459 | 2–3 |
| 37.3–37.7 | 2.410–2.386 | 0–2 |
| 39.7 | 2.271 | 0–1 |
| 40.9–41.1 | 2.206–2.196 | 0–1 |
| 43.85–44.1 | 2.065–2.054 | 0–1 |
| 46.1 | 1.969 | 0–1 |
| 47.4–47.7 | 1.918–1.908 | 0–1 |
| 49.7–49.8 | 1.834–1.831 | 0–1 |
| 51.4–51.7 | 1.778–1.768 | 0–1 |
| 52.2–52.45 | 1.752–1.745 | 0–1 |

EXAMPLE 56

(a) ZnAPSO-47, as referred to in example 38, was subjected to x-ray analysis. ZnAPSO-47 was determined to have a characteristic x-ray powder diffraction pattern which contains at least the d-spacings set forth below:

| 2θ | d, (Å) | 100 × I/Io |
|---|---|---|
| 7.45* | 11.88 | 2 |
| 9.45 | 9.35 | 93 |
| 12.9 | 6.87 | 17 |
| 13.9 | 6.38 | 7 |

-continued

| 2θ | d, (Å) | 100 × I/Io |
|---|---|---|
| 16.0 | 5.54 | 42 |
| 17.65 | 5.03 | 11 |
| 19.0* | 4.67 | 3 |
| 20.6 | 4.31 | 100 |
| 21.85 | 4.07 | 7 |
| 22.4* | 3.97 | 6 |
| 23.0 | 3.867 | 11 |
| 24.75 | 3.600 | 21 |
| 25.9 | 3.439 | 23 |
| 27.65 | 3.228 | 10 |
| 28.0 | 3.188 | 3 |
| 29.5 | 3.029 | 5 |
| 30.6 | 2.922 | 49 |
| 30.9 | 2.894 | sh |
| 31.5 | 2.839 | 3 |
| 32.3 | 2.772 | 2 |
| 33.3 | 2.689 | 3 |
| 34.5 | 2.600 | 10 |
| 34.9 | 2.573 | 2 |
| 35.7 | 2.516 | 4 |
| 38.4 | 2.344 | 3 |
| 39.65 | 2.273 | 4 |
| 42.5 | 2.126 | 3 |
| 43.3 | 2.089 | 2 |
| 44.9 | 2.019 | 2 |
| 47.6 | 1.909 | 4 |
| 48.6 | 1.873 | 5 |
| 50.5 | 1.807 | 5 |
| 53.25 | 1.721 | 5 |
| 54.5 | 1.684 | 2 |
| 56.0 | 1.642 | 5 |

*Impurity peak (b) A portion of the as-synthesized ZnAPSO-47 of part (a) was calcined in air at 500° C. for about 1.75 hours. The calcined product was characterized by the x-ray powder diffraction pattern below:

| 2θ | d, (Å) | 100 × I/Io |
|---|---|---|
| 7.5* | 11.78 | 11 |
| 9.65 | 9.17 | 100 |
| 13.05 | 6.78 | 25 |
| 14.15 | 6.26 | 3 |
| 16.2 | 5.46 | 10 |
| 18.0 | 4.93 | 8 |
| 19.25 | 4.61 | 3 |
| 19.8* | 4.49 | 2 |
| 20.85 | 4.26 | 27 |
| 21.25* | 4.18 | sh |
| 22.5* | 3.950 | 8 |
| 23.3 | 3.816 | 4 |
| 25.2 | 3.533 | 8 |
| 26.2 | 3.399 | 10 |
| 28.0 | 3.187 | 2 |
| 28.55 | 3.126 | 3 |
| 29.8 | 2.998 | 2 |
| 31.0 | 2.885 | 18 |
| 31.4 | 2.849 | sh |
| 34.9 | 2.571 | 2 |

*Impurity peak (c) The ZnAPSO-47 compositions are characterized by the date in Table XXV below:

TABLE XXV

| 2θ | d, (Å) | Relative Intensity |
|---|---|---|
| 9.45–9.65 | 9.35–9.17 | vs |
| 12.85–13.05 | 6.89–6.78 | w–m |
| 15.95–16.2 | 5.55–5.46 | w–m |
| 20.55–20.85 | 4.31–4.26 | m–vs |
| 25.9–26.2 | 3.439–3.399 | w–m |
| 30.55–31.0 | 2.925–2.885 | w–m |

(d) The ZnAPSO-47 compositions for which x-ray powder diffraction data have been obtained to date have patterns which are characterized by the x-ray powder diffraction pattern shown in Table XXVI below:

TABLE XXVI

| 2θ | d, (Å) | 100 × I/Io |
|---|---|---|
| 9.45–9.65 | 9.35–9.17 | 93–100 |
| 12.85–13.05 | 6.89–6.78 | 17–25 |
| 13.85–14.15 | 6.39–6.26 | 3–7 |
| 15.95–16.2 | 5.55–5.46 | 10–42 |
| 17.45–18.0 | 5.09–4.93 | 2–11 |
| 20.55–20.85 | 4.31–4.26 | 27–100 |
| 21.85 | 4.07 | 0–7 |
| 22.95–23.3 | 3.867–3.816 | 4–11 |
| 24.75–25.2 | 3.600–3.533 | 8–21 |
| 25.9–26.2 | 3.439–3.399 | 16–29 |
| 27.6–28.55 | 3.231–3.126 | 3–10 |
| 27.9–28.0 | 3.196–3.188 | 0–3 |
| 29.45–29.8 | 3.031–2.998 | 2–5 |
| 30.55–31.0 | 2.925–2.885 | 18–49 |
| 30.9–31.4 | 2.894–2.849 | sh |
| 31.5 | 2.839 | 0–3 |
| 32.3 | 2.772 | 0–2 |
| 33.3 | 2.689 | 0–3 |
| 34.45–34.9 | 2.603–2.600 | 2–19 |
| 34.9 | 2.573 | 0–2 |
| 35.7–35.9 | 2.516–2.503 | 0–5 |
| 38.4–38.55 | 2.344–2.336 | 0–3 |
| 39.6–39.65 | 2.273 | 0–4 |
| 42.25–42.5 | 2.139–2.126 | 0–3 |
| 43.3 | 2.089 | 0–2 |
| 44.9 | 2.019 | 0–2 |
| 47.6 | 1.909 | 0–6 |
| 48.6–48.7 | 1.873–1.870 | 0–5 |
| 50.45–50.5 | 1.807 | 0–5 |
| 53.2–53.25 | 1.722–1.721 | 0–5 |
| 54.5 | 1.684 | 0–2 |
| 56.0 | 1.642 | 0–5 |

EXAMPLE 57

In order to demonstrate the catlaytic activity of calcined ZnAPSO compositions were tested for catalytic cracking of n-butane using a bench-scale apparatus.

The reactor was a cylindrical quartz tube 254 mm. in length and 10.3 mm. I.D. In each test the reactor was loaded with particles of the test ZnAPSO which were 20–40 mesh (U.S. std.) in size and in an amount of from 0.5 to 5 grams, the quantity being selected so that the conversion of n-butane was at least 5% and not more than 90% under the test conditions. The ZnAPSO samples had been previously calcined in air to remove organic materials from the pore system, and were activated in situ in the reactor in a flowing stream of helium at 500° C. for one hour. The feedstock was a helium n-butane mixture containing 2 mole percent n-butane and was passed through the reactor at a rate of 50 cc./minute. Analysis of the feedstock and the reactor effluent were carried out using conventional gas chromatography techniques. The reactor effluent was analyzed after 10 minutes of on-stream operation.

The pseudo-first-order rate constant ($k_A$) was calculated to determine the relative catalytic activity of the ZnAPSO compositions. The $k_A$ value (cm³/g min) obtained for the ZnAPSO compositions are set forth, below, in Table XXVII:

TABLE XXVII

| ZnAPSO | Prepared in Example No. | Rate Constant $(k_A)$* |
|---|---|---|
| ZnAPSO-5 | 4 | 1.5 |
| ZnAPSO-34 | 24 | 12.7 |
| ZnAPSO-35 | 33 | 1.0 |
| ZnAPSO-44 | 35 | 5.0 |

TABLE XXVII-continued

| ZnAPSO | Prepared in Example No. | Rate Constant ($k_A$)* |
|---|---|---|
| ZnAPSO-47 | 39 | 5.6 |

*ZnAPSO were calcined prior to in situ activation as follows:
(a) ZnAPSO-5: in air at 500° C. for 0.75 and at 600° C. for 1.25 hours;
(b) ZnAPSO-34: in air at 500° C. for 2 hours;
(c) ZnAPSO-35: in air at 500° C. for 1.75 hours;
(d) ZnAPSO-44: in air at 500° C. for 67 hours; and
(e) ZnAPSO-47: in air at 500° C. for 1.75 hours.

PROCESS APPLICATIONS

The ZnAPSO compositions of the present invention are, in general, hydrophilic and adsorb water preferentially over common hydrocarbon molecules such as paraffins, olefins and aromatic species, e.g., benzene, xylenes and cumene. Thus, the ZnAPSOs as a class are useful as desiccants in such adsorption separation/-purification processes as natural gas drying, cracked gas drying. Water is also preferentially adsorbed over the so-called permanent gases such as carbon dioxide, nitrogen, oxygen and hydrogen. These ZnAPSOs are therefore suitably employed in the drying of reformer hydrogen streams and in the drying of oxygen, nitrogen or air prior to liquifaction.

The present ZnAPSO compositions also exhibit novel surface selectivity characteristics which render them useful as catalyst or catalyst bases in a number of hydrocarbon conversion and oxidative combustion reactions. They can be impregnated or otherwise loaded with catalytically active metals by methods well known in the art and used, for example, in fabricating catalyst compositions having silica or alumina bases. Of the general class, those species having pores larger than about 4Å are preferred for catalytic applications.

Among the hydrocarbon conversion reactions catalyzed by ZnAPSO compositions are cracking, hydrocracking, alkylation for both the aromatic and isoparaffin types, isomerization including xylene isomerization, polymerization, reforming, hydrogenation, dehydrogenation, transalkylation, dealkylation, hydrodecyclization and dehydrocyclization.

Using ZnAPSO catalyst compositions which contain a hydrogenation promoter such as platinum or palladium, heavy petroleum residual stocks, cyclic stocks and other hydrocrackable charge stocks, can be hydrocracked at temperatures in the range of 400° F. to 825° F. using molar ratios of hydrogen to hydrocarbon in the range of between 2 and 80, pressures between 10 and 3500 p.s.i.g., and a liquid hourly space velocity (LHSV) of from 0.1 to 20, preferably 1.0 to 10.

The ZnAPSO catalyst compositions employed in hydrocracking are also suitable for use in reforming processes in which the hydrocarbon feedstocks contact the catalyst at temperatures of from about 700° F. to 1000° F., hydrogen pressures of from 100 to 500 p.s.i.g., LHSV values in the range of 0.1 to 10 and hydrogen to hydrocarbon molar ratios in the range of 1 to 20, preferably between 4 and 12.

These same catalysts, i.e. those containing hydrogenation promoters, are also useful in hydroisomerizations processes in which feedstocks such a normal paraffins are converted to saturated branched chain isomers. Hydroisomerization is carried out at a temperature of from about 200° F. to 600° F., preferably 300° F. to 550° F. with an LHSV value of from about 0.2 to 1.0. Hydrogen is supplied to the reactor in admixture with the hydrocarbon feedstock in molar proportions (hydrogen to hydrocarbon) of between 1 and 5.

At somewhat higher temperatures, i.e. from about 650° F. to 1000° F., preferably 850° F. to 950° F. and usually at somewhat lower pressures within the range of about 15 to 50 p.s.i.g., the same catalyst compositions are used to hydroisomerize normal paraffins. Preferably the paraffin feedstock comprises normal paraffins having a carbon number range of $C_7$-$C_{20}$. Contact time between the feedstock and the catalyst is generally relatively short to avoid undesireable side reactions such as olefin polymerization and paraffin cracking. LHSV values in the range of 0.1 to 10, preferably 1.0 to 6.0 are suitable.

The unique crystal structure of the present ZnAPSO catalysts and their availability in a form totally void of alkali metal content favor their use in the conversion of alkylaromatic compounds, particularly the catalytic disproportionation of toluene, ethylene, trimethyl benzenes, tetramethyl benzenes and the like. In the disproportionation process, isomerization and transalkylation can also occur. Group VIII noble metal adjuvants alone or in conjunction with Group VI-B metals such as tungsten, molybdenum and chromium are preferably included in the catalyst composition in amounts of from about 3 to 15 weight-% of the overall composition. Extraneous hydrogen can, but need not, be present in the reactin zone which is maintained at a temperature of from about 400° to 750° F., pressures in the range of 100 to 2000 p.s.i.g. and LHSV values in the range of 0.1 to 15.

Catalytic cracking processes are preferably carried out with ZnAPSO compositions using feedstocks such as gas oils, heavy naphthas, deasphalted crude oil residua, etc., with gasoline being the pricipal desired product. Temperature conditions of 850° to 1100° F., LHSV values of 0.5 to 10 and pressure conditions of from about 0 to 50 p.s.i.g. are suitable.

Dehydrocyclization reactions employing paraffinic hydrocarbon feedstocks, preferably normal paraffins having more than 6 carbon atoms, to form benzene, xylenes, toluene and the like are carried out using essentially the same reaction conditions as for catalytic cracking. For these reactions it is preferred to use the ZnAPSO catalyst in conjunctin with a Group VIII non-noble metal cation such as zinc and nickel.

In catalytic dealkylation wherein it is desired to cleave paraffinic side chains from aromatic nuclei without substantially hydrogenating the ring structure, relatively high temperatures in the range of about 800°-1000° F. are employed at moderate hydrogen pressures of about 300-1000 p.s.i.g., other conditions being similar to those described above for catalytic hydrocracking. Preferred catalysts are of the same type described above in connection with catalytic dehydrocyclization. Particularly desirable dealkylation reactions contemplated herein include the conversion of methylnaphthalene to naphthalene and toluene and/or xylenes to benzene.

In catalytic hydrofining, the primary objective is to promote the selective hydrodecomposition of organic sulfur and/or nitrogen compounds in the feed, without substantially affecting hydrocarbon molecules therein. For this purpose it is preferred to employ the same general conditions described above for catalytic hydrocracking, and catalysts of the same general nature described in connection with dehydrocyclization operations. Feedstocks include gasoline fractions, kerosenes, jet fuel fractions, diesel fractions, light and heavy gas oils, deasphalted crude oil residua and the like any of which may contain up to about 5 weight-percent of sulfur and up to about 3 weight-percent of nitrogen.

Similar conditions can be employed to effect hydrofining, i.e., denitrogenation and desulfurization, of hydrocarbon feeds containing substantial proportions of organonitrogen and organosulfur compounds. It is generally recognized that the presence of substantial amounts of such constituents markedly inhibits the activity of hydrocracking catalysts. Consequently, it is necessary to operate at more extreme conditions when it is desired to obtain the same degree of hydrocracking conversion per pass on a relatively nitrogenous feed than are required with a feed containing less organonitrogen compounds. Consequently, the conditions under which denitrogenatin, desulfurization and/or hydrocracking can be most expeditiously accomplished in any given situation are necessarily determined in view of the characteristics of the feedstocks in particular the concentration of organonitrogen compounds in the feed stock. As a result of the effect of organonitrogen compounds on the hydrocracking activity of these compositions it is not at all unlikely that the conditions most suitable for denitrogenation of a given feedstock having a relatively high organonitrogen content with minimal hydrocracking, e.g., less than 20 volume percent of fresh feed per pass, might be the same as those preferred for hydrocracking another feedstock having a lower concentration of hydrocracking inhibiting constituents e.g., organonitrogen compounds. Consequently, it has become the practice in this art to establish the conditions under which a certain feed is to be contacted on the basis of preliminary screening tests with the specific catalyst and feedstock.

Isomerization reactions are carried out under conditions similar to those described above for reforming, using somewhat more acidic catalysts. Olefins are preferably isomerized at temperatures of 500°–900° F., while paraffins, naphthenes and alkyl aromatics are isomerized at temperatures of 700°–1000° F. Particularly desirable isomerization reactions contemplated herein include the conveersion of n-heptene and/or n-octane to isoheptanes, iso-octanes, butane to isobutane, methylcyclopentane to cyclohexane, metaxylene and/or ortho-xylene to paraxylene, 1-butene to 2-butene and/or isobutene, n-hexene to isohexene, cyclohexene to methylcyclopentene etc. The preferred from of the catalyst is a combination of the ZnAPSO with polyvalent metal compounds (such as sulfides) of metals of Group II-A, Group II-B and rare earth metals. For alkylation and dealkylation processes the ZaAPSO compositions having pores of at least 5A are preferred. When employed for dealkylation of alkyl aromatics, the temperature is usually at least 350° F. and ranges up to a temperaure at which substantial cracking of the feedstock or conversion products occurs, generally up to about 700° F. The temperature is preferably at least 450° F. and not greater than the critical temperature of the compound undergoing dealkylation. Pressure conditions are applied to retain at least the aromatic feed in the liquid state. For alkylation the temperature can be as low as 250° F. but is preferably at least 350° F. In the alkylatin of benzene, toluene and xylene, the preferred alkylating agents are olefins such as ethylene and propylene.

We claim:

1. Crystalline molecular sieves having three-dimensional microporous framework structures of $ZnO_2$, $AlO_2$, $PO_2$ and $SiO_2$ tetrahedral units having an empirical chemical composition on an anhydrous basis expressed by the formula:

$$Mr:(Zn_wAl_xP_ySi_z)O_2$$

wherein "R" represents at least one organic templating agent present in the intracrystalline pore system; "m" represents the molar amount of "R" present per mole of $(Zn_wAl_xP_ySi_z)O_2$ and has a value of zero (0) to about 0.3; and "w", "x", "y" and "z" represent the mole fractions of zinc, aluminum, phosphorus and silicon, respectively, present as tetrahedral oxides, said mole fractions being such that they are within the pentagonal compositional area defined by points A, B, C, D, and E of FIG. 1 and each has a value of at least 0.01.

2. Crystalline molecular sieves according to claim 1 wherein the mole fractions of zinc, aluminum, phosphorus and silicon present as tetrahedral oxides are within the tetragonal compositional area defined by points a, b, c and d of FIG. 2.

3. The crystalline molecular sieves of claims 1 or 2 having a characteristic x-ray powder deffraction pattern which contains at least the d-spacings set forth in Table A.

4. The crystalline molecular sieves of claims 1 or 2 having a characteristic x-ray powder diffraction pattern which contains at least the d-spacings set forth in Table B.

5. The crystalline molecular sieves of claim 1 or 2 having a characteristic x-ray powder diffraction pattern which contains at least the d-spacings set forth in Table C.

6. The crystalline molecular sieves of claims 1 or 2 having a characteristic x-ray powder diffraction pattern which contains at least the d-spacings set forth in Table D.

7. The crystalline molecular sieves of claims 1 or 2 having a characteristic x-ray powder diffraction pattern which contains at least the d-spacings set forth in Table E.

8. The crystalline molecular sieves of claims 1 or 2 having a characteristic x-ray powder diffraction pattern which contains at least the d-spacings set forth in the Table F.

9. The crystalline molecular sieves of claims 1 or 2 having a characteristic x-ray powder diffraction pattern which contains at least the d-spacings set forth in Table G.

10. The crystalline molecular sieves of claims 1 or 2 having a characteristic x-ray powder diffraction pattern which contains at least the d-spacings set forth in Table H.

11. The crystalline molecular sieves of claims 1 or 2 having a characteristic x-ray powder diffraction pattern which contains at least the d-spacings set forth in Table J.

12. The crystalline molecular sieves of claims 1 or 2 having a characteristic x-ray powder diffraction pattern which contains at least the d-spacings set forth in Table K.

13. The crystalline molecular sieves of claims 1 or 2 having a characteristic x-ray powder diffractions pattern which contains at least one d-spacing set forth in Table L.

14. The crystalline molecular sieves of claims 1 or 2 having a characteristic x-ray powder diffraction pattern which contains at least the d-spacings set forth in Table M.

15. Process for preparing crystalline molecular sieves having three-dimensional microporous framework structures of $ZnO_2$, $AlO_2$, $PO_2$, and $SiO_2$ tetrahedral units and having an empirical chemical composition on an anhydrous basis expressed by the formula:

$$mR:(Zn_wAl_xP_ySi_z)O_2$$

wherein "R" represents at least one organic templating agent present in the intracrystalline pore system; "m" represents the molar amount of "R" present per mole of $(Zn_wAl_xP_ySi_z)O_2$ and has a value between zero (0) to about 0.3; and "w", "x", "y", and "z" represent the mole fractions of zinc, aluminum, phosphorus, and silicon, respectively, present as tetrahedral oxides, said mole fractions being such that they are within the pentagonal compositional area defined by points A, B, C, D, and E of FIG. 1 and each has a value of at least 0.01; which comprises providing at an effective temperature and for an effective time a reaction mixture composition expressed in terms of molar oxide ratios as follows:

$$aR:(Zn_rAl_sP_tSi_y)O_2:bH_2O$$

wherein "R" is an organic templating agent; "a" is the amount of "R" and is an effective amount greater than zero to about 6.0; "b" has a value of from zero to about 500; and "r", "s", "t" and u represent mole fractions, respectively, of zinc, aluminum, phosphorus, and silicon in the $(Zn_rAl_sP_tSi_y)$ constituent, and each has a value of at least 0.01.

16. Process according to claim 15 wherein "r", "s", "t" and "u" are within the area defined by points F, G, H, I and J of FIG. 3.

17. Process according to claim 15 wherein the source of phosphorus in the reaction mixture is orthophosphoric acid.

18. Process according to claim 15 wherein the source of phosphorus in the reaction mixture is orthophosphoric acid and the source of aluminum is at least one compound selected from the group consisting of pseudo-boehmite and aluminum alkoxide.

19. Process according to claim 18 wherein the aluminum alkoxide is aluminum isopropoxide.

20. Process according to claim 15 wherein the source of silicon is silica.

21. Process according to claim 15 wherein the source of zinc is selected from the group consisting of oxides, hydroxides, alkoxides, acetates, nitrates, sulfates, carboxylates, organometallic zinc compounds and mixtures thereof.

22. Process according to claim 15 wherein the organic templating agent is a quaternary ammonium or quaternary phosphonium compound having the formula:

$$R_4X^+$$

wherein X is nitrogen or phosphorus and each R is an alkyl or aryl group containing from 1 to 8 carbon atoms.

23. Process according to claim 15 wherein the organic templating agent is an amine.

24. Process according to claim 15 wherein the templating agent is selected from the group consisting of tetrapropylammonium ion; tetraethylammonium ion; tripropylamine; triethylamine; triethanolamine; piperidine; cyclohexylamine; 2-methyl pyridine; N,N-dimethylbenzylamine; N,N-dimethylethanolamine; choline; N,N-dimethypiperazine; 1,4-diazabicyclo-(2,2,2) octane; N-methyldiethanolamine; N-methylethanolamine; n-methylpiperidine; 3-methylpiperidine; N-methylcyclohexylamine; 3-methylpyridine; 4-methylpyridine; quinuclidine; N,N'-dimethyl-1,4-diazabicyclo (2,2,2) octane ion; tetramethylammonium ion; tetrabutylammonium ion; tetrapentylammonium ion; di-n-butylamine; neopentylamine; di-n-pentylamine; isopropylamine; t-butylamine; ethylenediamine; pyrrolidine; 2-imidazolidone: di-n-propylamine; and a polymeric quaternary ammonium salt $[(C_{14}H_{32}N_2)(OH)_2]_x$ wherein x is a value of at least 2.

25. Molecular sieve prepared by calcining the composition of claim 1 or claim 2 at a temperature sufficiently high to remove at least some of the organic templating agent present in the intracrystalline pore system.

26. The crystalline molecular sieves of claims 1 or 2 wherein the values of "w" and "z" have the following mole fraction values: "w" is $\geq 0.03$; and "z" is $\geq 0.02$.

27. The process of claim 15 wherein "b" has a value of from about 2 to about 500.

28. The process of claim 27 wherein "b" has a value of from about 2 to about 300.

* * * * *